(12) United States Patent
Loughran et al.

(10) Patent No.: US 7,964,358 B2
(45) Date of Patent: Jun. 21, 2011

(54) SPHINGOSINE 1-PHOSPHATE RECEPTOR GENE, SPPR

(75) Inventors: Thomas P. Loughran, Hummelstown, PA (US); Ravi Kothapalli, Wesley Chapel, FL (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 12/879,918

(22) Filed: Sep. 10, 2010

(65) Prior Publication Data
US 2011/0021375 A1   Jan. 27, 2011

Related U.S. Application Data

(63) Continuation of application No. 12/193,428, filed on Aug. 18, 2008, now abandoned, which is a continuation of application No. 11/653,811, filed on Jan. 16, 2007, now abandoned, which is a continuation of application No. 10/024,019, filed on Dec. 21, 2001, now Pat. No. 7,220,580.

(60) Provisional application No. 60/257,119, filed on Dec. 22, 2000.

(51) Int. Cl.
*C12Q 1/68* (2006.01)
*G01N 33/53* (2006.01)
(52) U.S. Cl. ............................................ 435/6; 435/7.1
(58) Field of Classification Search ........................ None
See application file for complete search history.

(56) References Cited

U.S. PATENT DOCUMENTS

| | | | |
|---|---|---|---|
| 7,220,580 B2 | 5/2007 | Loughran et al. | |
| 2003/0119111 A1* | 6/2003 | Lal et al. | ...................... 435/69.1 |
| 2007/0105148 A1 | 5/2007 | Loughran et al. | |
| 2009/0181382 A1 | 7/2009 | Loughran et al. | |

FOREIGN PATENT DOCUMENTS

| | | |
|---|---|---|
| EP | 1 149 907 A1 | 10/2001 |
| WO | WO 97/00952 A2 | 1/1997 |
| WO | WO 99/33972 A1 | 7/1999 |
| WO | WO 99/46277 A1 | 9/1999 |
| WO | WO 00/11166 A1 | 3/2000 |
| WO | WO 00/31258 A2 | 6/2000 |
| WO | WO 01/66742 A2 | 9/2001 |
| WO | WO 02/57311 A3 | 7/2002 |

OTHER PUBLICATIONS

An et al., "Characterization of a Novel Subtype of Human G Protein-Coupled Receptor for Lysophosphatidad Acid*", *The Journal of Biological Chemistry* (1998), 273(14): 7906-7910.
An et al., "Signaling Mechanisms and Molecular Characteristics of G Protein-Coupled Receptors for Lysophosphatidic Acid and Sphingosine 1-Phosphate", *Journal of Cellular Biochemistry Supplements* (1998), 31:147-157.
Chen et al. "Discordant protein and mRNA expression in lung adenocarcinomas" *Molecular and Cellular Proteomics*, 2002, 1:304-313.
Database EMBL 'ONLINE! Dec. 6, 2000, retrieved from EBI Database accession No. af317676 XP002236901 abstract.
Database EMBL 'ONLINE! Oct. 8, 1999, retrieved from EBI Database accession No. ACO11461 XP002236899 abstract.
Database EMBL 'ONLINE! Sep. 28, 2001, retrieved from EBI Database accession No. AX244600 XP002236900 abstract (Sequence 26 from Patent WO 01 66742).
Epstein and Butow, "Microarray technology—enhanced versatility, persistent challenge", *Current Opinion in Biotechnology* (2000), 11: 36-41.
Glickman et al., "Molecular Cloning, Tissue-Specific Expression, and Chromosomal Localization of a Novel Nerve Growth Factor-Regulated G-Protein-Coupled Receptor, nrg-1", *Molecular and Cellular Neuroscience* (1999), 14:141-152.
Haynes et al. "Proteome analysis: biological assay or data archive?" *Electrophoresis*, 1998, 19:1862-1871.
HLA et al., "Sphingosine-1-Phosphate Signaling via the EDG-1 Family of G-Protein-Coupled Receptors", *Annals New York Academy of Sciences* (2000), 905:16-24.
Hu et al. "Analysis of genomic and proteomic data using advanced literature mining" *J. Proteome Res.*, 2003, 2:405-412.
Im et al., "Characterization of a Novel Sphingosine 1-Phosphate Receptor, Edg-8*", *The Journal of Biological Chemistry* (2000), 275(19):14281-14286.
Im, D.S. et al. "Characterization of the human and mouse sphingosine 1-phosphate receptor, S1P5(Edg-8): Structure-activity relationship of sphingosine 1-phosphate receptors" *Biochem.*, 2001, 40:14053-060.
IM, D.S. et al. as cited in: http://www.ncbi.nlm.nih.gov/entrez/query.fcgi?cmd=Retrieve&db=nucleotide&list_uids=18141314& dopt=GenBank "1:NM_030760.Homo sapiens endo . . .", Jan. 13, 2002, p. 1-3.
IM, D.S. et al. as cited in: http://www.ncbi.nlm.nih.gov/entrez/query.fcgi?cmd=Retrieve&db=nucleotide&list_uids=18141314& dopt=GenBank "1:NM_030760[gi:13540516]", Dec. 10, 2001, p. 1-2.
Kothapalli, et al., "Characterization of Human Sphingosine-1-Phosphate Receptor Gene (S1P5) and its Differential Expression in LGL Leukemia", *Biochemica et Biophysica Acta* (2002), 117-123..
Kothapalli, R. et al. "Characterization of a novel human sphingosine-1-phosphate receptor gene (sppr) and its differential expression in LGL leukemia" *Blood: Gene Expression in Lymphoid Malignancy*, 2001, 98:3029. Kothapalli, R. et al. as cited in: http://www.ncbi.nlm.nih.gov/entrez/query.fcgi?cmd=Retrieve&db=nucleotide&list$_{13}$ uids=18033256& dopt=GenBank "1:AF331840.Homo sapiens SPPR . . .", Jan. 2, 2002, p. 1-2.
Kothapalli, R. at al. as cited in: http://www.ncbi.nlm.nih.gov/entrez/query.fcgi?cmd=Retrieve&db=nucleotide&list_uids=18033258& dopt=GenBank "1:AF331841.Homo sapiens SPPR. . .", Jan. 2, 2002, p. 1-2.
Kothapalli, R. et al. as cited in: http://www.ncbi.nlm.nih.gov/entrez/query.fcgi?cmd=Retrieve&db=nucleotide&list_uids=180 33260& dopt=GenBank "1:AF331842.Homo sapiens SPPR . . .", Jan. 2, 2002, p. 1-2.
Malek, R. et al. "Nrg-1 belongs to the endothelial differentiation gene family of G protein-coupled sphingosine-1-phosphate receptors" *J. Biol. Chem.*, 2001, 276(8):5692-99.
Semenzato et al., The Lymphoproliferative Disease of Granular Lymphocytes: Updated Criteria for Diagnosis, *Blood* (1997), 89(1): 256-260.

* cited by examiner

*Primary Examiner* — Christine J Saoud
*Assistant Examiner* — Jon M Lockard
(74) *Attorney, Agent, or Firm* — Saliwanchik, Lloyd & Eisenschenk

(57) ABSTRACT

A novel sphingosine 1-phosphate receptor gene, herein termed sppr, and its splice variants. Sppr is up-regulated in LGL and is useful, for example, in the diagnosis and treatment of certain lymphoproliferative, neurodegenerative and autoimmune diseases.

7 Claims, 16 Drawing Sheets

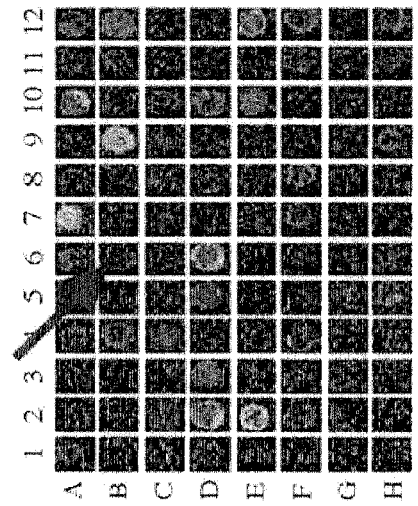
FIG. 1B Normal
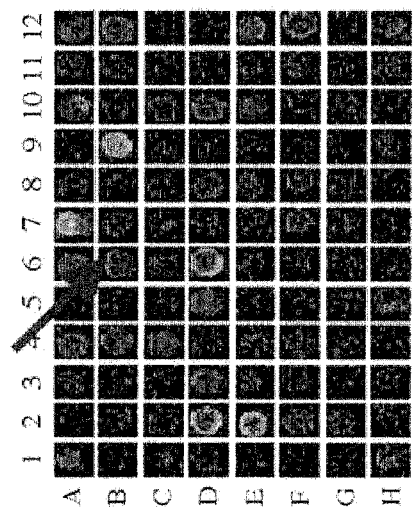
FIG. 1A LGL
Microarray
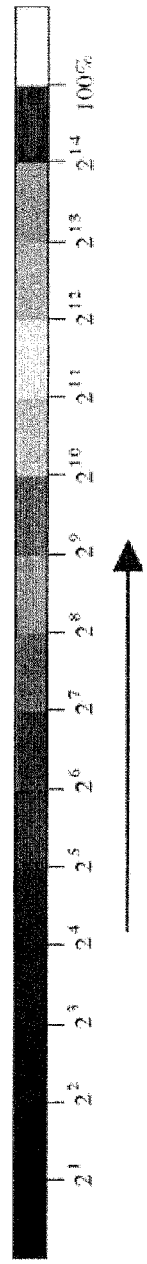

FIG. 3

```
Human sphingosine 1-Phosphate receptor
LOCUS       tmpseq_1      2336 bp                              4-DEC-2000
SOURCE      PBMCs (LGL)
  ORGANISM  Human
            Unclassified.
FEATURES            Location/Qualifiers
     source         1..2336
     CDS            10..1206,10..1206
                    /note="predicted coding region"
                    /translation="

MESGLLRPAPVSEVIVLHYNYTGKLRGARYQPGAGLRADAVVCLAVCAFIVLENLAVLLV
LGRHPRFHAPMFLLLGSLTLSDLLAGAAYAANILLSGPLTLKLSPALWFAREGGVFVALT
ASVLSLLAIALERSLTMARRGPAPVSSRGRTLAMAAAAWGVSLLLGLLPALGWNCLGRLD
ACSTVLPLYAKAYVLFCVLAFVGILAAICALYARIYCQVRANARRLPARPGTAGTTSTRA
RRKPRSLALLRTLSVVLLAFVACWGPLFLLLLLDVACPARTCPVLLQADPFLGLAMANSL
LMPIIYTLTNRDLRHALLRLVCCGRHSCGRDPSGSQQSASAAEASGGLRRCLPPGLDGSF
SGSERSSPQRDGLDTSGSTGSPGAPTAARTLVSEPAAD"

BASE COUNT     461 a    679 c    701 g    495 t
ORIGIN
        1 gcgcggccca tggagtcggg gctgctgcgg ccggcgtcgg tgagcgaggt catcgtcctg
       61 cattacaact acaccggcaa gctccgcggt gcgcgctacc agcccggtgc cggcctgcgc
      121 gccgacgccg tggtgtgcct ggcggtgtgc gccttcatcg tgctagagaa tctagccgtg
      181 ttgttggtgc tggacgcca cccgcgcttc cacgctccca tgttcctgct cctgggcagc
      241 ctcacgttgt cggatctgct ggcaggcgcc gctacgcgg ccaacatcct actgtcgggg
      301 ccgctcacgc tgaaactgtc ccccgcgctc tggttcgcac gggaggagg cgtcttcgtg
      361 gcactcactg cgtccgtgct gagcctcctg gccatcgcgc tggagcgcag cctcaccatg
      421 gcgcgcaggg gcccgcgcc cgtctccagt cgggggcgca cgctggcgat ggcagccgcg
      481 gccgggggcg tgtcgctgct cctcgggctc ctgccagcgc tgggctggaa ttgcctgggt
      541 cgcctgcacg cttgatccac tgtcttgccg ctctacgca aggcctacgt gctcttctgc
      601 gtgctcgcct cgtgggcat cctggcgcg atctgtgcac tctacgcg catctactgc
      661 caggtacgcg ccaacgcgcg gcgcctgccg gcacggcccg ggactgcggg gaccacctcg
      721 accgggcgc gtcgcaagcc gcgctgctg gccttgctgc gcacgctcag cgtggtgctc
      781 ctggcttttg tggcatgttg ggggcccctc ttcctgctgc tgttgctcga cgtggcgtgc
      841 ccggcgcgca cctgctcgt actcctgcag gccgatccct tcctgggact ggccatggcc
      901 aactcactc tgaacccat catctacacg ctcaccaacc gcgacctgcg ccacgcgctc
      961 ctgcgcctgg tctgctgggg acgccactcc tgcggcagag acccgagtgg ctcccagcag
     1021 tcggcgagcg cggctgaggc ttccggggc ctgcgcgct gcctgccccc gggccttgat
     1081 gggagcttca gcggctcgga gcgctcatcg cccagcgcg acgggctgga caccagcggc
     1141 tccataggca gcccggtgc acccacgcc gcccggactc tggtatcaga accggctgca
     1201 gactgacacc ctcggcccac gactgtcttc ccaagttttta cagacttgtt cttttttacat
     1261 aaaggaattt gtaggaaatg cagccaaagg tgcagtcgga aaagatgcag gggaaatgta
     1321 tttatgcagc gacacccac aatgtgaaca aacagacaaa aatctgtcc cctcgtggaa
     1381 ttgacgttct gcttgggaac acagaaaaga actcggtgat gaaataatgg agatgattcc
     1441 agtgacaaac gacagagatg gtgatggtgg tcagggaaga cctctctgca gaggtagtga
     1501 cctgtgatgt gagctgagac ctctgtcctg ggaagaccaa aagaaaagca tttcaggatg
     1561 agggaatggc atgcgcaaag gccctgaggc tgaaatgtgc ccatgtgttc taagaaatgc
     1621 agcgatgctg gcgtgcctgg agcagggacg gaggggagaa atgggaggag caacgagct
     1681 gaaggagtag ttcccgaagg acccttgtgg tgatatagag gacttcgctt ttgctctgag
     1741 tgaggtcgga gccatagaag ctctcaagca gaagagggac ttgccctaat tcaggtgatc
     1801 acaggtgtct tgtggcctcc atgggaggtt gaaaaccaca gaaggtgaag ggggctgca
     1861 ctgagccaca ggaacaatga tggagattcc agctaagccc agacccgtg gattcctagat
     1921 agatttaga ggcagcagac agaattactg aggaatgag tgtaagagtg gaataaagtt
     1981 atcaaggaca atgccaaggg tgggctaccc ccaaatttga cttttgggaga ctcagccaaa
     2041 tcctatctgg taataaaatt tctttttttat tttcttttct tttctttctt tcttcttttc
     2101 tttttttttt ttgagttgg gatcttgtgc tctgtcaacc aggctggagt gcaatgggca
     2161 caattatagc tcactgcagc ctggaactcc tgggatcaag cctgagttc ctgcttcagc
     2221 ctcctagta gctgggacta caggcatgca ccaccatgcc cagttaataa aatttcttca
     2281 aatgcaaaaa aaaaaaaaaa aaaaactcg aggggggggcc cggtacccaa ttcgcc
//
```

Alignment of deduced Amino acid sequence with Nrg-1 and Edg-8 (rat genes)

```
Nrg-1    MESGLLRPAPVSEVIVLHYNYTGKLRGARYQPGAGLRADAAVCLAVCAFIVLEHLAVLLV
EDG-8    MESGLLRPAPVSEVIVLHYNYTGKLRGARYQPGAGLRADAAVCLAVCAFIVLENIAVLLV
SPPR     MESGLLRPAPVSEVIVLHYNYTGKLRGARYQPCAGLRADAVVCLAVCAFIVLEHLAVLLV
         *********************************:*******.*************

Nrg-1    LGRHPRFHAPMFLLLGSLTLSDLLAGAAYATHILLSGPLTLRLSPALMFAREGGVFVALA
EDG-8    LGRHPRFHAPMFLLLGSLTLSDLLAGAAYATHILLSGPLTLRLSPALMFAREGGVFVALA
SPPR     LGRHPRFHAPMFLLLGSLTLSDLLAGAAVAANILLSGPLTLKLSPALMFAREGGVFVALT
         *************************  * :******** :**************.

Nrg-1    ASVLSLLAIAIERHLTMARRGPAPAASRARTLAMAVAAWGLLLTLGLLPALGWNCLGRLE
EDG-8    ASVLSLLAIALERHLTMARRGPAPAASRARTLAMAVAAWGLSLLLGLLPALGWNCLGRLE
SPPR     ASVLSLLAIALERSLTMARRGPAPVSSRGRTLAMAAAAWGVSLLLGL PALGWNCLGRLD
         **********:** **********.::** ****** :****:**:** ***********

Nrg-1    ACSTVLPVYAKAYVLFCVLAFIGILAAICALYARIYCQVRANARRLRAGPGSRRATSSSR
EDG-8    ACSTVLPLYAKAYVLFCVLAFLGILAAICALYARIYCQVRANARRLRAGPGSRRATSSSR
SPPR     ACSTVLPLYAKAYVLFCVLAFVGILAAICALYARIYCQVRANARRLPARFGT-AGTTSTR
         *******:*************:************************  *: .  *:**:*

Nrg-1    SRHTPRSLALLRTLSVVLLAFVACWGPLFLLLLLDVACPARACPVLLQADPFLGLAMANS
EDG 8    SRHTPRSLALLRTLSVLLAFVACWGPLFLLLLLDVACPARACPVLLQADPFLGLAMANS
SPPR     ARRLPRSLALLRTLSVLLAFVACWGPLFLLLLLDVACPARTCPVLLQADPFLGLAMANS
         :*: ***********.***********************.************ ********

Nrg 1    LLMPIIYTFTNRDLRHALLRLLCCGRGCNQDSNSLQRSPSAVGPSGGLRRCLPPTLD
EDG-8    LLMPIIYTFTNRDLRHALLRLLCCGRGCNQDSNSLQRSPSAVGPSGGGLRRCLPPTLD
SPPR     LLMPIIYTLTNRDLRHALLRLLWCCGRHSCGRDPSGSQQ--SASAEASGG-LRRCLPPGLD
         ********:************  ****:  * **  .*     . : : * ****** **

Nrg-1    RSSSPSEHSCPQRDGMDTSCSTGSPGAATANRTLVPDATD
EDG-8    RSSSPSEHSCFQRDGMDISCSTGSPGAATNJRTLVPDATD--
SPPR     GSFSGSERSSPQRDGLDTSGSTGSPGAPTAARTLVSEPAAD
         . : *. * : ***  * * ******* :  **:. ..:*
```

SPPR: Nrg ~85%
SPPR: EDG ~86%
* - single, fully conserved residue
: - conservation of strong groups
. - conservation of weak groups
- - no consensus

```
Sphingosine-1- phosphate receptor.1
LOCUS       tmpseq_1    1698 bp                                    30-OCT-2000
DEFINITION  No definition line found.
ACCESSION   tmpseq_1
VERSION
KEYWORDS    .
SOURCE      Unknown.
  ORGANISM  Unknown.
            Unclassified.
FEATURES             Location/Qualifiers
     source          1..1698
     CDS             11..775,11..775
                     /note="predicted coding region"
                     /translation="MESGLLRPAPVSEVIVLHYNYTGKLRGARYQPGAGLRADAVVCL
                     AVCAFIVLENLAVLLVLGRHPRFHAPMFLLLGSLTLSVPARPGTAGTTSTRARRKPRS
                     LALLRTLSVVLLAFVACWGPLFLLLLLDVACPARTCPVLQADPFLGLAMANSLLNPI
                     IYTLTNRDLRHALLRLVCCGRHSCGRDPSGSQQSASAAEASGGLRRCLPPGLDGSFSG
                     SERSSPQRDGLDTSGSTGSPGAPTAARTLVSEPAAD"
BASE COUNT      352 a    462 c    516 g    368 t
ORIGIN
        1 cgcgcggccc atggagtcgg ggctgctgcg gccggcgccg gtgagcgagg tcatcgtcct
       61 gcattacaac tacacggtca agctccgcgg tgcgcgctac cagccgggtg ccggcctgcg
      121 cgccgacgcc gtggtgtgcc tggcggtgtg cgccttcatc gtgctagaga atctagccgt
      181 gttgttggtg ctcggacgcc accgcgctt ccacgctcc atgttcctgc tcctgggcag
      241 cctcacgttg tcggtgcgg cacggccgg gactgcgggg accacctcga cccgggcgcg
      301 tcgcaagccg cgctcgctgg ccttgctgcg cacgctcagc gtggtgctcc tggcctttgt
      361 ggcatgtgg ggcccctct tcctgctgct gttgctcgac gtggcgtgcc cggcgcgcac
      421 ctgtcctgta ctcctgcagg ccgatccctt cctgggactg gccatggcca actcacttct
      481 gaaccccatc atctacacgc tcaccaaccg cgacctgcgc cacgcgctcc tgcgcctggt
      541 ctgctgcgga cgccactcct gcggcagaga cccgagtggc tcccagcagt cggcgagcgc
      601 ggctgaggct tccggggcc tgcgcgctg cctgccccg ggcctgatg ggagcttcag
      661 cggctcggag cgctcatcgc cccagcgcga cgggctggac accagtggct ccacaggcag
      721 ccccggtgca cccacagccg cccggactct ggtatcagaa ccggctgcag actgacaccc
      781 tcggccacg actgtcttcc caagtttac agacttgttc tttttacata aaggaatttg
      841 taggaaatgc agccaaaggt gcagtcggaa aagatgcagg ggaaatgtat ttatgcagcg
      901 atacccccaca atgtgaacaa acagacaaaa aatctgtgcc ctgtggaat tgacgttctg
      961 cttgggaaca cagaaaagaa ctcggtgatg aaataatgga gatgattcca gtgacaaacg
     1021 acagagatgg tgatggtggt cagggaagac ctctctgcag aggtagtgac ttgtgatgtg
     1081 agctgaactc tctgtcctgg gaagaccaaa agaaaagcat ttcaggatga gggaatggca
     1141 tgcgcaaagg ccctgaggct gaaatgtgcc catgtgttct aagaaatgca gcgatgctgg
     1201 tgtgctgga gcaggacgg aggggagaa tgggaggaga caaggagctg aaggagtagt
     1261 tcccgaagga ccttgtgggt gatatagagg acttcgcttt tgctctgagt gaggtgggag
     1321 ccatagaagc ttctaagcag aagagggact tgccctaatt caggtgatca caggtgtctt
     1381 gtggcctcca tggaggttg aaaccagag aaggtgaagg ggggctgcac tgagccacag
     1441 gaacaatgat ggagattcca gctaagccca gacccgtgga attctagata gattttagag
     1501 gcagcagaca gaattactga ggaattgagt gtaagagtgg aataaagtta tcaaggacaa
     1561 tgccaagggt gggcacccc caaatttgac tctgggagac tcagccaaat cctatctggt
     1621 aataaaattc cttttttatt ttctcttct tccttcttt cttttttt ttttgagtt
     1681 gggatcttct gctctgtc
//
```

FIG. 6

Sphingosine-1-Phosphate receptor 2

```
LOCUS       tmpseq_1     1245 bp                              30-OCT-2000
DEFINITION  No definition line found.
ACCESSION   tmpseq_1
VERSION
KEYWORDS    .
SOURCE      Unknown.
  ORGANISM  Unknown.
            Unclassified.
FEATURES             Location/Qualifiers
     source          1..1245
     CDS             11..322,11..322
                     /note="predicted coding region"
                     /translation="MESGLLRPAPVSEVIVLHYNYTGKLRGARYQPGAGLRADAVVCL
                     AVCAFIVLENLAVLLVLGRHPRFHAPMFLLLGSLTLSDLLAGAAYAAAARTLVSEPAA
                     D"
BASE COUNT      298 a    284 c    372 g    291 t
ORIGIN
        1 cgcgcggccc atggagtcgg ggctgctgcg gccggcgccg gtgagcgagg tcatcgtcct
       61 gcattacaac tacaccggca agctccgcgg tgcgcgctac cagccgggtg cgggcctgcg
      121 cgccgacgcc gtggtgtgcc tggcggtgtg cgccttcatc gtgctagaga atctagccgt
      181 gctgttggtg ctcggacgcc acccgcgctt ccacgctccc atgttcctgc tcctgggcag
      241 cctcacgttg tcggatctgc tggcaggcgc cgcctacgcc gcgccgccc  ggactctggt
      301 atcagaaccg gctgcagact gacaccctcg gcccacgact gtcttcccaa gttttacaga
      361 cctgttctct ttacataaag gaatttgtag gaaatgcagc caaggtgca  gtcggaaaag
      421 atgcagggga aatgtattta tgcagcgaca ccccacaatg tgaacaaaca gacaaaaaat
      481 ctgtgccctc gtggaattga cgttctgctt gggaacacag aaaagaactc ggtgatgaaa
      541 taatggagat gattccagtg acaaacgaca gagatggtga tggtggtcag ggaagacctc
      601 tctgcagagg tagtcgacttg tgatctgagc tgagacctct gtcctgggaa gaccaaaaga
      661 aaagcattc  aggatgaggg aatggcatgc gcaaaggccc tgaggctgaa atgtgccat
      721 gtgttctaag aaatgcagcg atgctggtgt gcctggagca gggacggagg gggagaatgg
      781 gaggagacaa ggagctgaag gagtagttcc cgaaggacct tgtgggtgat atagaggact
      841 tgctttttgc tctgagtgag gtcggagcca tagaagcttc taagcagaag agggacttgc
      901 cctaattcag gtgatcacag gtgtcttgtg gcctccatgg gaggttgaaa accagagaag
      961 gtgaaggggg gctgtactga gccacaggaa caatgatgga gattccagct aagcccagac
     1021 ccgtggatt  ctagatagat tttagaggca gcagacagaa ttactgagga attgagtgta
     1081 agagtggaat aaagttatca aggacaatgc caagggtggg gcaccccaa  atttgactct
     1141 gggagactca gccaaatct  atctggtaat aaaattcctt ttctattttt ctttttcttt c
     1201 ttctttcttc tttttttttt  tgagttggg atcttgtgct ctgtc
```

```
   1 gcgcggccatcgagtcgggcctgctgcggccggcgccggtgagcgaggtcatcgtcctg
     M  E  S  G  L  L  R  P  A  P  V  S  E  V  I  V  L      17
  61 cattacaactacaccggcaagctccgcggtgcgcgctaccagccgggtgccggcctgcgc
     H  Y  N  Y  T  G  K  L  R  G  A  R  Y  Q  P  G  A  G  L  R   37
 121 gccgacgccgtcgtgtgcctcgcggtgtgcgccttcatcgtgctagagaatctagccgtg
     A  D  A  V  V  C  L  A  V  C  A  F  I  V  L  E  N  L  A  V   57
 181 ttgttggtgctcggacgccacccgcgcttccacgctccatgttcctgctcctgggcagc
     L  L  V  L  G  R  H  P  R  F  H  A  P  M  F  L  L  L  G  S   77
 241 ctcacgttgtcggatctgctggcaggcgccgcctacgccgccaacatcctactgtcgggg
     L  T  L  S  D  L  A  G  A  A  Y  A  A  N  I  L  L  S  G   97
 301 ccgctcacgctgaaactgtccccgcgctctggttcgcacgggagggaggcgtcttcgtg
     P  L  T  L  K  L  S  P  A  L  W  F  A  R  E  G  G  V  F  V  117
 361 gcactcactgcgtccgtgctgagcctcctggccatcgcgctggagcgcagcctcaccatg
     A  L  T  A  S  V  L  S  L  L  A  I  A  L  E  R  S  L  T  M  137
 421 gcgcgcaggggggccgcgccgtctccagtcggggcgcacgctggcgatggcagccgcg
     A  R  R  G  P  A  P  V  S  S  R  G  R  T  L  A  M  A  A  A  157
 481 gcctggggcgtgtcgctgctcctcgggctcctgccagcgctgggctggaattgcctgggt
     A  W  G  V  S  L  L  G  L  L  P  A  L  G  W  N  C  L  G  177
 541 cgcctggacgcttgctccactgtcttgccgctctacgccaaggcctacgtgctcttctgc
     R  L  D  A  C  S  T  V  L  P  L  Y  A  K  A  Y  V  L  F  C  197
 601 gtgctcgccttcgtgggcatcctggccgcgatctgtgcactctacgcgcgcatctactgc
     V  L  A  F  V  G  I  L  A  A  I  C  A  L  Y  A  R  I  Y  C  217
 661 caggtacgcgccaacgcgcggcgcctgccggcacggcccgggactgcggggaccacctcg
     Q  V  R  A  N  A  R  R  L  P  A  R  P  G  T  A  G  T  T  S  237
 721 acccggcgcgtcgcgaaccgcgctcgctggccttgctgcgcacgctcagcgtggtgctc
     T  R  A  R  R  K  P  R  S  L  A  L  L  R  T  L  S  V  V  L  257
 781 ctggcctttgtggcatgttgggccccctcttcctgctgctgttgctcgacgtggcgtgc
     L  A  F  V  A  C  W  G  P  L  F  L  L  L  L  D  V  A  C  277
 841 ccggcgcacctgtcctgtactcctgcaggcgcgatccttcctgggactggccatggcc
     P  A  R  T  C  P  V  L  L  Q  A  D  P  F  L  G  L  A  M  A  297
 901 aactcacttctgaaccccatcatctacacgctcaccaaccgcgacctcgcgccacgcgct
     N  S  L  L  N  P  I  I  Y  T  L  T  N  R  D  L  R  H  A  L  317
 961 ctgcgcctggtctgctgcggacgccactcctgcggcagagacccgagtggctcccagcag
     L  R  L  V  C  C  G  R  H  S  C  G  R  D  P  S  G  S  Q  Q  337
1021 tcggcgagcgcggctgaggcttccgggggcctgcgccgctgcctgcccccgggccttgat
     S  A  S  A  A  E  A  S  G  G  L  R  R  C  L  P  P  G  L  D  357
1081 gggagcttcagcggctcggagcgctcatcgccccagcgcgacgggctggacaccagcggc
     G  S  F  S  G  S  E  R  S  S  P  Q  R  D  G  L  D  T  S  G  377
1141 tccacaggcagccccggtgcacccacagccgccggactctggtatcagaaccggctgca
     S  T  G  S  P  G  A  P  T  A  A  R  T  L  V  S  E  P  A  A  397
1201 gactgacaccctcggccacgactgtcttcccaagttttacagacttgttctttttacat
     D  *                                                         398
1261 aaaggaatttgtaggaaatgcagccaaggtgcagtcggaaaagatgcaggggaaatgta
1321 tttatgcagcgacaccccacaatgtgaacaaacagacaaaaaatctgtgccctcgtggaa
1381 ttgacgttctgcttgggaacacagaaaagaactcggtgatgaaataatggagatgattcc
1441 agtgacaaacgacagagatggtgatggtggtcagggaagacctctctgcagaggtagtga
1501 cttgtgatgtgagctgagacctctgtcctggcgaagacaaaagaaaagcatttcaggatg
1561 agggaatggcatgcgcaaaggccctgaggctgaaatgtgcccatgtgttctaagaaatgc
1621 agcgatgctggtgtgcctggagcagggacggaggggggagaatggaggagacaaggagct
1681 gaaggagtagttcccgaaggaccttgtgggtgatatagaggacttccttttgctctgag
1741 tgaggtgggagccatagaagcttctaagcagaagagggacttgccctaattcaggtgatc
1801 acaggtgtcttgtggcctccatgggaggttgaaaaccacagaaggtgaaggggggctgca
1861 ctgagccacaggaacaatgatggagattccagctaagcccagaccccgtggattctagat
1921 agattttagaggcagcagacagaattactgaggaattgagtgtaagagtggaataaagtt
1981 atcaaggacaatgccaagggtggggcaccccaaatttgactttggcagactcagccaaa
2041 tcctatctggtaataaaatttcttttttatttttctttctttctttctttctttctttc
2101 ttttttttttttgagttgggatcttgtgctctgtcacccaggctgcagtgcaatgggca
2161 caattatagctcactgcagcctgcaactcctgggatcaagcctgagttcctgcttcagc
2221 ctccctagtagctgggactacaggcatgcaccaccatgcccagttaataaaattcttca
2281 aatgcaaaaaaaaaaaaaaaaaaaaaa
```

FIG. 8

```
NRG-1  MESGLLRPAPVSEVIVLHYNYTGKLRGARYQPGAGLRADAAVCLAVCAFIVLENLAVLLV
EDG-β  MESGLLRPAPVSEVIVLHYNYTGKLRGARYQPGAGLRADAAVCLAVCAFIVLENLAVLLV
SIP₅   MESGLLRPAPVSEVIVLHYNYTGKLRGARYQPGAGLRADAVVCLAVCAFIVLENLAVLLV
       ***********************************************************

NRG-1  LGRHPRFHAPMFLLLGSLTLSDLLAGAAYATNILLSGPLTLRLSPALWFAREGGVFVALA
EDG-β  LGRHPRFHAPMFLLLGSLTLSDLLAGAAYATNILLSGPLTLRLSPALWFAREGGVFVALA
SIP₅   LGRHPRFHAPMFLLLGSLTLSDLLAGAAYAANILLSGPLTLKLSPALWFAREGGVFVALT
       *****************************:*********:****************** :

NRG-1  ASVLSLLAIAIERHLTMARRGPAPAASRARTLAMAVAAWGLLLTLGLLPALGWNCLGRLE
EDG-β  ASVLSLLAIALERHLTMARRGPAPAASRARTLAMAVAAWGLSLLLGLLPALGWNCLGRLE
SIP₅   ASVLSLLAIALERSLTMARRGPAPVSSRGRTLAMAAAAWGVSLLLGLLPALGWNCLGRLD
       **********:** **********.:** ******.****: * ***************:

NRG-1  ACSTVLPVYAKAYVLFCVLAFLGILAAICALYARIYCQVRANARRLRAGPGSRRATSSSR
EDG-β  ACSTVLPLYAKAYVLFCVLAFLGILAAICALYARIYCQVRANARRLRAGPGSRRATSSSR
SIP₅   ACSTVLPLYAKAYVLFCVLAFVGILAAICALYARIYCQVRANARRLPARPGT-AGTTSTR
       *******:*************:***********************  * **:  .*:*:*

NRG-1  SRHTPRSLALLRTLSVVLLAFVACWGPLFLLLLLDVACPARACPVLLQADPFLGLAMANS
EDG-β  SRHTPRSLALLRTLSVVLLAFVACWGPLFLLLLLDVACPARACPVLLQADPFLGLAMANS
SIP₅   ARRKPRSLALLRTLSVVLLAFVACWGPLFLLLLLDVACPARTCPVLLQADPFLGLAMANS
       :*:.*****************************************:*************

NRG-1  LLNPIIYTFTNRDLRHALLRLLCCGRGPCNQDSSNSLQRSPSAVGPSGGGLRRCLPPTLD
EDG-β  LLNPIIYTFTNRDLRHALLRLLCCGRGPCNQDSSNSLQRSPSAVGPSGGGLRRCLPPTLD
SIP₅   LLNPIIYTLTNRDLRHALLRLVCCGRHSCGRDPSGSQQ-SASAAEASGG-LRRCLPPGLD
       ********:************:****  .*:*.*.* * *.**. .*** ******* **

NRG-1  RSSSPSEHSCPQRDGMDTSCSTGSPGAATANRTLVPDATD-
EDG-β  RSSSPSEHSCPQRDGMDTSCSTGSPGAATANRTLVPDATD-
SIP₅   GSFSGSERSSPQRDGLDTSGSTGSPGAPTAARTLVSEPAAD
       * * *:  *.*****:*** ******* ** ****.::.:

SIP₅: Nrg - 85%
S1P5: ECG - 86%
* - single, fully conserved residue
: - conservation of strong groups
. - conservation of weak groups
  - no consensus
```

FIG. 9

```
SIP5    MESGLLRPAPVSEVIVLHYNYTGKLRGARYQPGAGLRADAVVCLAVCAFIVLENLAVLLV
SIP5-α  MESGLLRPAPVSEVIVLHYNYTGKLRGARYQPGAGLRADAVVCLAVCAFIVLENLAVLLV
        ************************************************************

SIP5    LGRHPREFHAPMFLLLGSLTLSDLLAGAAYAANILLSGPLTLKLSPALWFAREGGVFVALT
SIP5-α  LGRHPREFHAPMFLLLGSLTLS--------------------------------------
        *********************

SIP5    ASVLSLLAIALERSLTMARRGPAPVSSRGRTLAMAAAAWGVSLLLGLLPALGWNCLGRLD
SIP5-α  ------------------------------------------------------------

SIP5    ACSTVLPLYAKAYVLFCVLAFVGILAAICALYARIYCQVRANARRLPARPGTAGTTSTRA
SIP5-α  ---------------------------------------VPARPGTAGTTSTRA
                                                :: ***************

SIP5    RRKPRSLALIRTLSVVLLAFVACWGPLFLILLLDVACPARTCPVLLQADPFLGLAMANSL
SIP5-α  RRKPRSLALIRTLSVVLLAFVACWGPLFLILLLDVACPARTCPVLLQADPFLGLAMANSL
        ************************************************************

SIP5    LNPIIYTLTNRDLRHALLRLVCCGRHSCGRDPSGSQQSASAAEASGGLRRCLPPGLDGSF
SIP5-α  LNPIIYTLTNRDLRHALLRLVCCGRHSCGRDPSGSQQSASAAEASGGLRRCLPPGLDGSF
        ************************************************************

SIP5    SGSERSSPQRDGLDTSGSTGSPGAPTAARTLVSEPAAD
SIP5-α  SGSERSSPQRDGLDTSGSTGSPGAPTAARTLVSEPAAD
        **************************************
```

FIG. 12A

```
S1P5    MESGLLRPAPVSEVIVLHYNYTGKLRGARYQPGAGLRADAVVCLAVCAFIVLENLAVLLV
S1P5-β  MESGLLRPAPVSEVIVLHYNYTGKLRGARYQPGAGLRADAVVCLAVCAFIVLENLAVLLV
        ************************************************************

S1P5    LGRHPRFHAPMFLLLGSLTLSDLLAGAAYAANILLSGPLTLKLSPALWFAREGGVFVALT
S1P5-β  LGRHPRFHAPMFLLLGSLTLSDLLAGAAYAA-----------------------------
        *******************************

S1P5    ASVLSLLAIALERSLTMARRGPAPVSSRGRTLAMAAAAWGVSLLLGLLPALGWNCLGRLD
S1P5-β  ------------------------------------------------------------

S1P5    ACSTVLPLYAKAYVLFCVLAFVGILAAICALYARTYCQVRANARRLPARPGTAGTTSTRA
S1P5-β  ------------------------------------------------------------

S1P5    RRKPRSLALLRTLSVVLLAFVACWGPLFLLLLLDVACPARTCPVLLQADPFLGLAMANSL
S1P5-β  ------------------------------------------------------------

S1P5    LNPIIYTLTNRDLRHALLRLVCCGRHSCGRDPSGSQQSASAAEASGGLRRCLPPGLDGSF
S1P5-β  ------------------------------------------------------------

S1P5    SGSERSSPQRDGLDTSGSTGSPGAPTAARTLVSEPAAD
S1P5-β  ---------------------------AARTLVSEPAAD
                                   ************
```

FIG. 12B

```
S1P   MESGLLRPAPVSEVIVLHYNYTGKLRGARYQPGAGLRADAVVCLAVCAFIVLENLAVLLV
S1P1  MESGLLRPAPVSEVIVLHYNYTGKLRGARYQPGAGLRADAVVCLAVCAFIVLENLAVLLV
      ************************************************************

S1P   LGRHPRFHAPMFLLLGSLTLSDLLAGAAYAANILLSGPLTLKLSPALWFAREGCVFVALT
S1P1  LGRHPRFHAPMFLLLGSLTLS---------------------------------------
      *********************

S1P   ASVLSLLAIALERSLTMARRGPAPVSSRGRTLAMAAAAWGVSLLLGLLPALGWNCLGRLD
S1P1  ------------------------------------------------------------

S1P   ACSTVLPLYAKAYVLFCVLAFVGILAAICALYARIYCQVRANARRLPARPGTAGTTSTRA
S1P1  ---------------------------------------VPARPGTAGTTSTRA
                                             *******************

S1P   RRKPRSLALLRTLSVVLLAFVACWGPLFLLLLLDVACPARTCPVLLQADPFLGLAMANSL
S1P1  RRKPRSLALLRTLSVVLLAFVACWGPLFLLLLLDVACPARTCPVLLQADPFLGLAMANSL
      ************************************************************

S1P   LNPIIYTLTNRDLRHALLRLVCCGRHSCGRDPSGSQQSASAAEASCGLRRCLPPGLDGSF
S1P1  LNPIIYTLTNRDLRHALLRLVCCGRHSCGRDPSGSQQSASAAEASCGLRRCLPPGLDGSF
      ************************************************************

S1P   SGSERSSPQRDGLDTSGSTGSPGAPTAARTLVSEPAAD
S1P1  SGSERSSPQRDGLDTSGSTGSPGAPTAARTLVSEPAAD
      *************************************

S1P= Sphingosine-1-Phosphate receptor versus
S1P1=Sphingosine-1-Phosphate 1 receptor
```

FIG. 14

```
SIP   MESGLLRPAPVSEVIVLHYNYTGKLRGARYQPGAGLRADAVVCLAVCAFIVLENLAVLLV
SIP2  MESGLLRPAPVSEVIVLHYNYTGKLRGARYQPGAGLRADAVVCLAVCAFIVLENLAVLLV
      ************************************************************

SIP   LGRHPRFHAPMFLLLGSLTLSDLLAGAAYAANILLSGPLTLKLSPALWFAREGGVFVALT
SIP2  LGRHPRFHAPMFLLLGSLTLSDLLAGAAYAA-----------------------------
      ******************************

SIP   ASVLSLLAIALERSLTMARRGPAPVSSRGRTLAMAAAAWGVSLLLGLLPALGWNCLGRLD
SIP2  ------------------------------------------------------------

SIP   ACSTVLPLYAKAYVLFCVLAFVGILAAICALYARIYCQVRANARRLPARPGTAGTTSTRA
SIP2  ------------------------------------------------------------

SIP   RRKPRSLALLRTLSVVLLAFVACWGPLFLLLLLDVACPARTCPVLLQADPFLGLAMANSL
SIP2  ------------------------------------------------------------
SIP   LNPIIYTLTNRDLRHALLRLVCCGRHSCGRDPSGSQQSASAAEASGGLRRCLPPGLDGSF
SIP2  ------------------------------------------------------------
SIP   SGSERSSPQRDGLDTSGSTGSPGAPTAARTLVSEPAAD
SIP2  -----------------------AARTLVSEPAAD
                             ***********
```

FIG. 15

SEQUENCE LISTING

```
<160> NUMBER OF SEQ ID NOS: 19

<210> SEQ ID NO 1
<211> LENGTH: 17
<212> TYPE: DNA
<213> ORGANISM: Artificial Sequence
<220> FEATURE:
<223> OTHER INFORMATION: Probe (see p. 8 of specification)

<400> SEQUENCE: 1
gcgcggccca tggagtc                                                   17

<210> SEQ ID NO 2
<211> LENGTH: 30
<212> TYPE: DNA
<213> ORGANISM: Artificial Sequence
<220> FEATURE:
<223> OTHER INFORMATION: Probe (see p. 8 of specification)

<400> SEQUENCE: 2
cttttctgtg ttcccaagca gaacgtcaat                                     30

<210> SEQ ID NO 3
<211> LENGTH: 398
<212> TYPE: PRT
<213> ORGANISM: Homo sapiens
<220> FEATURE:
<221> NAME/KEY: MISC_FEATURE
<223> OTHER INFORMATION: Human sphingosine 1-Phosphate receptor (SPPR)
      amino acid sequence (Figure 3)
```

```
<400> SEQUENCE: 3

Met Glu Ser Gly Leu Leu Arg Pro Ala Pro Val Ser Glu Val Ile Val
1               5                   10                  15

Leu His Tyr Asn Tyr Thr Gly Lys Leu Arg Gly Ala Arg Tyr Gln Pro
            20                  25                  30

Gly Ala Gly Leu Arg Ala Asp Ala Val Val Cys Leu Ala Val Cys Ala
        35                  40                  45

Phe Ile Val Leu Glu Asn Leu Ala Val Leu Leu Val Leu Gly Arg His
    50                  55                  60

Pro Arg Phe His Ala Pro Met Phe Leu Leu Gly Ser Leu Thr Leu
65                  70                  75                  80

Ser Asp Leu Leu Ala Gly Ala Ala Tyr Ala Ala Asn Ile Leu Leu Ser
                85                  90                  95

Gly Pro Leu Thr Leu Lys Leu Ser Pro Ala Leu Trp Phe Ala Arg Glu
            100                 105                 110

Gly Gly Val Phe Val Ala Leu Thr Ala Ser Val Leu Ser Leu Leu Ala
        115                 120                 125

Ile Ala Leu Glu Arg Ser Leu Thr Met Ala Arg Arg Gly Pro Ala Pro
130                 135                 140

Val Ser Ser Arg Gly Arg Thr Leu Ala Met Ala Ala Ala Trp Gly
145                 150                 155                 160

Val Ser Leu Leu Leu Gly Leu Leu Pro Ala Leu Gly Trp Asn Cys Leu
                165                 170                 175

Gly Arg Leu Asp Ala Cys Ser Thr Val Leu Pro Leu Tyr Ala Lys Ala
            180                 185                 190

Tyr Val Leu Phe Cys Val Leu Ala Phe Val Gly Ile Leu Ala Ala Ile
        195                 200                 205

Cys Ala Leu Tyr Ala Arg Ile Tyr Cys Gln Val Arg Ala Asn Ala Arg
210                 215                 220

Arg Leu Pro Ala Arg Pro Gly Thr Ala Gly Thr Thr Ser Thr Arg Ala
225                 230                 235                 240

Arg Arg Lys Pro Arg Ser Leu Ala Leu Leu Arg Thr Leu Ser Val Val
                245                 250                 255

Leu Leu Ala Phe Val Ala Cys Trp Gly Pro Leu Phe Leu Leu Leu Leu
            260                 265                 270

Leu Asp Val Ala Cys Pro Ala Arg Thr Cys Pro Val Leu Leu Gln Ala
        275                 280                 285

Asp Pro Phe Leu Gly Leu Ala Met Ala Asn Ser Leu Leu Asn Pro Ile
    290                 295                 300

Ile Tyr Thr Leu Thr Asn Arg Asp Leu Arg His Ala Leu Leu Arg Leu
305                 310                 315                 320

Val Cys Cys Gly Arg His Ser Cys Gly Arg Asp Pro Ser Gly Ser Gln
                325                 330                 335

Gln Ser Ala Ser Ala Ala Glu Ala Ser Gly Gly Leu Arg Arg Cys Leu
            340                 345                 350

Pro Pro Gly Leu Asp Gly Ser Phe Ser Gly Ser Glu Arg Ser Ser Pro
        355                 360                 365

Gln Arg Asp Gly Leu Asp Thr Ser Gly Ser Thr Gly Ser Pro Gly Ala
    370                 375                 380

Pro Thr Ala Ala Arg Thr Leu Val Ser Glu Pro Ala Ala Asp
385                 390                 395

<210> SEQ ID NO 4
<211> LENGTH: 2336
```

```
<212> TYPE: DNA
<213> ORGANISM: Homo sapiens
<220> FEATURE:
<221> NAME/KEY: MISC_FEATURE
<223> OTHER INFORMATION: Human sphingosine 1-Phosphate receptor (SPPR)
      cDNA sequence (Figure 3)

<400> SEQUENCE: 4
```

| | | | | |
|---|---|---|---|---|
| gcgcggccca | tggagtcggg | gctgctgcgg | ccggcgccgg | tgagcgaggt | catcgtcctg |   60 |
| cattacaact | acaccggcaa | gctccgcggt | gcgcgctacc | agccgggtgc | cggcctgcgc |  120 |
| gccgacgccg | tggtgtgcct | ggcggtgtgc | gccttcatcg | tgctagagaa | tctagccgtg |  180 |
| ttgttggtgc | tcggacgcca | cccgcgcttc | cacgctccca | tgttcctgct | cctgggcagc |  240 |
| ctcacgttgt | cggatctgct | ggcaggcgcc | gcctacgccg | ccaacatcct | actgtcgggg |  300 |
| ccgctcacgc | tgaaactgtc | ccccgcgctc | tggttcgcac | gggagggagg | cgtcttcgtg |  360 |
| gcactcactg | cgtccgtgct | gagcctcctg | gccatcgcgc | tggagcgcag | cctcaccatg |  420 |
| gcgcgcaggg | ggcccgcgcc | cgtctccagt | cgggggcgca | cgctggcgat | ggcagccgcg |  480 |
| gcctggggcg | tgtcgctgct | cctcgggctc | ctgccagcgc | tgggctggaa | ttgcctgggt |  540 |
| cgcctggacg | cttgctccac | tgtcttgccg | ctctacgcca | aggcctacgt | gctcttctgc |  600 |
| gtgctcgcct | tcgtgggcat | cctggccgcg | atctgtgcac | tctacgcgcg | catctactgc |  660 |
| caggtacgcg | ccaacgcgcg | gcgcctgccg | gcacggcccg | ggactgcggg | gaccacctcg |  720 |
| acccgggcgc | gtcgcaagcc | gcgctcgctg | gccttgctgc | gcacgctcag | cgtggtgctc |  780 |
| ctggcctttg | tggcatgttg | gggccccctc | ttcctgctgc | tgttgctcga | cgtggcgtgc |  840 |
| ccggcgcgca | cctgtcctgt | actcctgcag | gccgatccct | tcctgggact | ggccatggcc |  900 |
| aactcacttc | tgaaccccat | catctacacg | ctcaccaacc | gcgacctgcg | ccacgcgctc |  960 |
| ctgcgcctgg | tctgctgcgg | acgccactcc | tgcggcagag | acccgagtgg | ctcccagcag | 1020 |
| tcggcgagcg | cggctgaggc | ttccggggcg | ctgcgccgct | gcctgccccc | gggccttgat | 1080 |
| gggagcttca | gcggctcgga | gcgctcatcg | ccccagcgcg | acgggctgga | caccagcggc | 1140 |
| tccacaggca | gccccggtgc | acccacagcc | gcccggactc | tggtatcaga | accggctgca | 1200 |
| gactgacacc | ctcggcccac | gactgtcttc | ccaagtttta | cagacttgtt | cttttacat | 1260 |
| aaaggaattt | gtaggaaatg | cagccaaagg | tgcagtcgga | aaagatgcag | gggaaatgta | 1320 |
| tttatgcagc | gacaccccac | aatgtgaaca | aacagacaaa | aaatctgtgc | cctcgtggaa | 1380 |
| ttgacgttct | gcttgggaac | acagaaaaga | actcggtgat | gaaataatgg | agatgattcc | 1440 |
| agtgacaaac | gacagagatg | gtgatggtgg | tcagggaaga | cctctctgca | gaggtagtga | 1500 |
| cttgtgatgt | gagctgagac | ctctgtcctg | ggaagaccaa | aagaaaagca | tttcaggatg | 1560 |
| agggaatggc | atgcgcaaag | gccctgaggc | tgaaatgtgc | ccatgtgttc | taagaaatgc | 1620 |
| agcgatgctg | gtgtgcctgg | agcagggacg | gaggggagga | atgggaggag | acaaggagct | 1680 |
| gaaggagtag | ttcccgaagg | accttgtggg | tgatatagag | gacttcgctt | ttgctctgag | 1740 |
| tgaggtggga | gccatagaag | cttctaagca | gaagagggac | ttgccctaat | tcaggtgatc | 1800 |
| acaggtgtct | tgtggcctcc | atgggaggtt | gaaaaccaca | gaaggtgaag | ggggctgca | 1860 |
| ctgagccaca | ggaacaatga | tggagattcc | agctaagccc | agaccccgtg | gattctagat | 1920 |
| agattttaga | ggcagcagac | agaattactg | aggaattgag | tgtaagagtg | gaataaagtt | 1980 |
| atcaaggaca | atgccaaggg | tggggcaccc | ccaaatttga | ctttgggaga | ctcagccaaa | 2040 |
| tcctatctgt | taataaaatt | tcttttttat | ttttctttt | tttctttctt | tctttctttc | 2100 |
| tttttttt | tttgagttgg | gatcttgtgc | tctgtcaccc | aggctggagt | gcaatgggca | 2160 |

```
caattatagc tcactgcagc ctggaactcc tgggatcaag cctggagttc ctgcttcagc    2220
ctccctagta gctgggacta caggcatgca ccaccatgcc cagttaataa aatttcttca    2280
aatgcaaaaa aaaaaaaaaa aaaaaactcg agggggggcc cggtacccaa ttcgcc        2336
```

<210> SEQ ID NO 5
<211> LENGTH: 400
<212> TYPE: PRT
<213> ORGANISM: Rattus norvegicus
<220> FEATURE:
<221> NAME/KEY: MISC_FEATURE
<223> OTHER INFORMATION: Nrg-1 rat genes (Figure 4)

<400> SEQUENCE: 5

```
Met Glu Ser Gly Leu Leu Arg Pro Ala Pro Val Ser Glu Val Ile Val
1               5                   10                  15

Leu His Tyr Asn Tyr Thr Gly Lys Leu Arg Gly Ala Arg Tyr Gln Pro
            20                  25                  30

Gly Ala Gly Leu Arg Ala Asp Ala Ala Val Cys Leu Ala Val Cys Ala
        35                  40                  45

Phe Ile Val Leu Glu Asn Leu Ala Val Leu Leu Val Leu Gly Arg His
    50                  55                  60

Pro Arg Phe His Ala Pro Met Phe Leu Leu Leu Gly Ser Leu Thr Leu
65                  70                  75                  80

Ser Asp Leu Leu Ala Gly Ala Ala Tyr Ala Thr Asn Ile Leu Leu Ser
                85                  90                  95

Gly Pro Leu Thr Leu Arg Leu Ser Pro Ala Leu Trp Phe Ala Arg Glu
            100                 105                 110

Gly Gly Val Phe Val Ala Leu Ala Ala Ser Val Leu Ser Leu Leu Ala
        115                 120                 125

Ile Ala Ile Glu Arg His Leu Thr Met Ala Arg Arg Gly Pro Ala Pro
    130                 135                 140

Ala Ala Ser Arg Ala Arg Thr Leu Ala Met Ala Val Ala Ala Trp Gly
145                 150                 155                 160

Leu Leu Leu Thr Leu Gly Leu Leu Pro Ala Leu Gly Trp Asn Cys Leu
                165                 170                 175

Gly Arg Leu Glu Ala Cys Ser Thr Val Leu Pro Val Tyr Ala Lys Ala
            180                 185                 190

Tyr Val Leu Phe Cys Val Leu Ala Phe Leu Gly Ile Leu Ala Ala Ile
        195                 200                 205

Cys Ala Leu Tyr Ala Arg Ile Tyr Cys Gln Val Arg Ala Asn Ala Arg
    210                 215                 220

Arg Leu Arg Ala Gly Pro Gly Ser Arg Arg Ala Thr Ser Ser Ser Arg
225                 230                 235                 240

Ser Arg His Thr Pro Arg Ser Leu Ala Leu Leu Arg Thr Leu Ser Val
                245                 250                 255

Val Leu Leu Ala Phe Val Ala Cys Trp Gly Pro Leu Phe Leu Leu Leu
            260                 265                 270

Leu Leu Asp Val Ala Cys Pro Ala Arg Ala Cys Pro Val Leu Leu Gln
        275                 280                 285

Ala Asp Pro Phe Leu Gly Leu Ala Met Ala Asn Ser Leu Leu Asn Pro
    290                 295                 300

Ile Ile Tyr Thr Phe Thr Asn Arg Asp Leu Arg His Ala Leu Leu Arg
305                 310                 315                 320

Leu Leu Cys Cys Gly Arg Gly Pro Cys Asn Gln Asp Ser Ser Asn Ser
                325                 330                 335
```

-continued

Leu Gln Arg Ser Pro Ser Ala Val Gly Pro Ser Gly Gly Gly Leu Arg
        340                 345                 350

Arg Cys Leu Pro Pro Thr Leu Asp Arg Ser Ser Pro Ser Glu His
        355                 360                 365

Ser Cys Pro Gln Arg Asp Gly Met Asp Thr Ser Cys Ser Thr Gly Ser
370                 375                 380

Pro Gly Ala Ala Thr Ala Asn Arg Thr Leu Val Pro Asp Ala Thr Asp
385                 390                 395                 400

<210> SEQ ID NO 6
<211> LENGTH: 400
<212> TYPE: PRT
<213> ORGANISM: Rattus norvegicus
<220> FEATURE:
<221> NAME/KEY: MISC_FEATURE
<223> OTHER INFORMATION: EDG-8 rat genes (Figure 4)

<400> SEQUENCE: 6

Met Glu Ser Gly Leu Leu Arg Pro Ala Pro Val Ser Glu Val Ile Val
1                   5                   10                  15

Leu His Tyr Asn Tyr Thr Gly Lys Leu Arg Gly Ala Arg Tyr Gln Pro
            20                  25                  30

Gly Ala Gly Leu Arg Ala Asp Ala Ala Val Cys Leu Ala Val Cys Ala
        35                  40                  45

Phe Ile Val Leu Glu Asn Leu Ala Val Leu Val Leu Gly Arg His
    50                  55                  60

Pro Arg Phe His Ala Pro Met Phe Leu Leu Gly Ser Leu Thr Leu
65                  70                  75                  80

Ser Asp Leu Leu Ala Gly Ala Ala Tyr Ala Thr Asn Ile Leu Leu Ser
                85                  90                  95

Gly Pro Leu Thr Leu Arg Leu Ser Pro Ala Leu Trp Phe Ala Arg Glu
            100                 105                 110

Gly Gly Val Phe Val Ala Leu Ala Ala Ser Val Leu Ser Leu Leu Ala
        115                 120                 125

Ile Ala Leu Glu Arg His Leu Thr Met Ala Arg Arg Gly Pro Ala Pro
130                 135                 140

Ala Ala Ser Arg Ala Arg Thr Leu Ala Met Ala Val Ala Ala Trp Gly
145                 150                 155                 160

Leu Ser Leu Leu Leu Gly Leu Pro Ala Leu Gly Trp Asn Cys Leu
                165                 170                 175

Gly Arg Leu Glu Ala Cys Ser Thr Val Leu Pro Leu Tyr Ala Lys Ala
            180                 185                 190

Tyr Val Leu Phe Cys Val Leu Ala Phe Leu Gly Ile Leu Ala Ala Ile
        195                 200                 205

Cys Ala Leu Tyr Ala Arg Ile Tyr Cys Gln Val Arg Ala Asn Ala Arg
    210                 215                 220

Arg Leu Arg Ala Gly Pro Gly Ser Arg Arg Ala Thr Ser Ser Ser Arg
225                 230                 235                 240

Ser Arg His Thr Pro Arg Ser Leu Ala Leu Leu Arg Thr Leu Ser Val
                245                 250                 255

Val Leu Leu Ala Phe Val Ala Cys Trp Gly Pro Leu Phe Leu Leu Leu
            260                 265                 270

Leu Leu Asp Val Ala Cys Pro Ala Arg Ala Cys Pro Val Leu Leu Gln
        275                 280                 285

Ala Asp Pro Phe Leu Gly Leu Ala Met Ala Asn Ser Leu Leu Asn Pro
    290                 295                 300

```
Ile Ile Tyr Thr Phe Thr Asn Arg Asp Leu Arg His Ala Leu Leu Arg
305                 310                 315                 320

Leu Leu Cys Cys Gly Arg Gly Pro Cys Asn Gln Asp Ser Ser Asn Ser
            325                 330                 335

Leu Gln Arg Ser Pro Ser Ala Val Gly Pro Ser Gly Gly Gly Leu Arg
            340                 345                 350

Arg Cys Leu Pro Pro Thr Leu Asp Arg Ser Ser Ser Pro Ser Glu His
            355                 360                 365

Ser Cys Pro Gln Arg Asp Gly Met Asp Thr Ser Cys Ser Thr Gly Ser
            370                 375                 380

Pro Gly Ala Ala Thr Ala Asn Arg Thr Leu Val Pro Asp Ala Thr Asp
385                 390                 395                 400

<210> SEQ ID NO 7
<211> LENGTH: 398
<212> TYPE: PRT
<213> ORGANISM: Homo sapiens
<220> FEATURE:
<221> NAME/KEY: MISC_FEATURE
<223> OTHER INFORMATION: SPPR (Figure 4)

<400> SEQUENCE: 7

Met Glu Ser Gly Leu Leu Arg Pro Ala Pro Val Ser Glu Val Ile Val
1               5                   10                  15

Leu His Tyr Asn Tyr Thr Gly Lys Leu Arg Gly Ala Arg Tyr Gln Pro
            20                  25                  30

Gly Ala Gly Leu Arg Ala Asp Ala Val Val Cys Leu Ala Val Cys Ala
            35                  40                  45

Phe Ile Val Leu Glu Asn Leu Ala Val Leu Leu Val Leu Gly Arg His
    50                  55                  60

Pro Arg Phe His Ala Pro Met Phe Leu Leu Leu Gly Ser Leu Thr Leu
65                  70                  75                  80

Ser Asp Leu Leu Ala Gly Ala Ala Tyr Ala Ala Asn Ile Leu Leu Ser
                85                  90                  95

Gly Pro Leu Thr Leu Lys Leu Ser Pro Ala Leu Trp Phe Ala Arg Glu
            100                 105                 110

Gly Gly Val Phe Val Ala Leu Thr Ala Ser Val Leu Ser Leu Leu Ala
            115                 120                 125

Ile Ala Leu Glu Arg Ser Leu Thr Met Ala Arg Arg Gly Pro Ala Pro
130                 135                 140

Val Ser Ser Arg Gly Arg Thr Leu Ala Met Ala Ala Ala Ala Trp Gly
145                 150                 155                 160

Val Ser Leu Leu Leu Gly Leu Leu Pro Ala Leu Gly Trp Asn Cys Leu
                165                 170                 175

Gly Arg Leu Asp Ala Cys Ser Thr Val Leu Pro Leu Tyr Ala Lys Ala
            180                 185                 190

Tyr Val Leu Phe Cys Val Leu Ala Phe Val Gly Ile Leu Ala Ala Ile
            195                 200                 205

Cys Ala Leu Tyr Ala Arg Ile Tyr Cys Gln Val Arg Ala Asn Ala Arg
            210                 215                 220

Arg Leu Pro Ala Arg Pro Gly Thr Ala Gly Thr Thr Ser Thr Arg Ala
225                 230                 235                 240

Arg Arg Lys Pro Arg Ser Leu Ala Leu Leu Arg Thr Leu Ser Val Val
                245                 250                 255

Leu Leu Ala Phe Val Ala Cys Trp Gly Pro Leu Phe Leu Leu Leu Leu
            260                 265                 270
```

```
Leu Asp Val Ala Cys Pro Ala Arg Thr Cys Pro Val Leu Leu Gln Ala
            275                 280                 285

Asp Pro Phe Leu Gly Leu Ala Met Ala Asn Ser Leu Leu Asn Pro Ile
            290                 295                 300

Ile Tyr Thr Leu Thr Asn Arg Asp Leu Arg His Ala Leu Leu Arg Leu
305                 310                 315                 320

Val Cys Cys Gly Arg His Ser Cys Gly Arg Asp Pro Ser Gly Ser Gln
            325                 330                 335

Gln Ser Ala Ser Ala Ala Glu Ala Ser Gly Gly Leu Arg Arg Cys Leu
            340                 345                 350

Pro Pro Gly Leu Asp Gly Ser Phe Ser Gly Ser Glu Arg Ser Ser Pro
            355                 360                 365

Gln Arg Asp Gly Leu Asp Thr Ser Gly Ser Thr Gly Ser Pro Gly Ala
            370                 375                 380

Pro Thr Ala Ala Arg Thr Leu Val Ser Glu Pro Ala Ala Asp
385                 390                 395

<210> SEQ ID NO 8
<211> LENGTH: 254
<212> TYPE: PRT
<213> ORGANISM: Homo sapiens
<220> FEATURE:
<221> NAME/KEY: MISC_FEATURE
<223> OTHER INFORMATION: Sphingosine-1-phosphate receptor.1 (Figure 5)

<400> SEQUENCE: 8

Met Glu Ser Gly Leu Leu Arg Pro Ala Pro Val Ser Glu Val Ile Val
1               5                   10                  15

Leu His Tyr Asn Tyr Thr Gly Lys Leu Arg Gly Ala Arg Tyr Gln Pro
            20                  25                  30

Gly Ala Gly Leu Arg Ala Asp Ala Val Val Cys Leu Ala Val Cys Ala
            35                  40                  45

Phe Ile Val Leu Glu Asn Leu Ala Val Leu Leu Val Leu Gly Arg His
    50                  55                  60

Pro Arg Phe His Ala Pro Met Phe Leu Leu Leu Gly Ser Leu Thr Leu
65                  70                  75                  80

Ser Val Pro Ala Arg Pro Gly Thr Ala Gly Thr Thr Ser Thr Arg Ala
            85                  90                  95

Arg Arg Lys Pro Arg Ser Leu Ala Leu Leu Arg Thr Leu Ser Val Val
            100                 105                 110

Leu Leu Ala Phe Val Ala Cys Trp Gly Pro Leu Phe Leu Leu Leu Leu
            115                 120                 125

Leu Asp Val Ala Cys Pro Ala Arg Thr Cys Pro Val Leu Leu Gln Ala
            130                 135                 140

Asp Pro Phe Leu Gly Leu Ala Met Ala Asn Ser Leu Leu Asn Pro Ile
145                 150                 155                 160

Ile Tyr Thr Leu Thr Asn Arg Asp Leu Arg His Ala Leu Leu Arg Leu
            165                 170                 175

Val Cys Cys Gly Arg His Ser Cys Gly Arg Asp Pro Ser Gly Ser Gln
            180                 185                 190

Gln Ser Ala Ser Ala Ala Glu Ala Ser Gly Gly Leu Arg Arg Cys Leu
            195                 200                 205

Pro Pro Gly Leu Asp Gly Ser Phe Ser Gly Ser Glu Arg Ser Ser Pro
            210                 215                 220

Gln Arg Asp Gly Leu Asp Thr Ser Gly Ser Thr Gly Ser Pro Gly Ala
225                 230                 235                 240
```

Pro Thr Ala Ala Arg Thr Leu Val Ser Glu Pro Ala Ala Asp
                245                 250

<210> SEQ ID NO 9
<211> LENGTH: 1698
<212> TYPE: DNA
<213> ORGANISM: Homo sapiens
<220> FEATURE:
<221> NAME/KEY: misc_feature
<223> OTHER INFORMATION: Sphingosine-1-phosphate receptor.1 (Figure 5)

<400> SEQUENCE: 9

| | | | | | |
|---|---|---|---|---|---|
| cgcgcggccc | atggagtcgg | ggctgctgcg | gccggcgccg | gtgagcgagg | tcatcgtcct | 60 |
| gcattacaac | tacaccggca | agctccgcgg | tgcgcgctac | cagccgggtg | ccggcctgcg | 120 |
| cgccgacgcc | gtggtgtgcc | tggcggtgtg | cgccttcatc | gtgctagaga | atctagccgt | 180 |
| gttgttggtg | ctcggacgcc | acccgcgctt | ccacgctccc | atgttcctgc | tcctgggcag | 240 |
| cctcacgttg | tcggtgccgg | cacggcccgg | gactgcgggg | accacctcga | cccgggcgcg | 300 |
| tcgcaagccg | cgctcgctgg | ccttgctgcg | cacgctcagc | gtggtgctcc | tggcctttgt | 360 |
| ggcatgttgg | ggccccctct | tcctgctgct | gttgctcgac | gtggcgtgcc | cggcgcgcac | 420 |
| ctgtcctgta | ctcctgcagg | ccgatccctt | cctgggactg | ccatggcca | actcacttct | 480 |
| gaacccatc | atctacacgc | tcaccaaccg | cgacctgcgc | cacgcgctcc | tgcgcctggt | 540 |
| ctgctgcgga | cgccactcct | gcggcagaga | cccgagtggc | tcccagcagt | cggcgagcgc | 600 |
| ggctgaggct | tccgggggcc | tgcgccgctg | cctgccccg | ggccttgatg | ggagcttcag | 660 |
| cggctcggag | cgctcatcgc | cccagcgcga | cgggctggac | accagcggct | ccacaggcag | 720 |
| ccccggtgca | cccacagccg | cccggactct | ggtatcagaa | ccggctgcag | actgacaccc | 780 |
| tcggcccacg | actgtcttcc | caagttttac | agacttgttc | ttttacata | aaggaatttg | 840 |
| taggaaatgc | agccaaaggt | gcagtcggaa | aagatgcagg | ggaaatgtat | ttatgcagcg | 900 |
| acacccccaca | atgtgaacaa | acagacaaaa | aatctgtgcc | ctcgtggaat | tgacgttctg | 960 |
| cttgggaaca | cagaaaagaa | ctcggtgatg | aaataatgga | gatgattcca | gtgacaaacg | 1020 |
| acagagatgg | tgatggtggt | cagggaagac | ctctctgcag | aggtagtgac | ttgtgatgtg | 1080 |
| agctgagacc | tctgtcctgg | gaagaccaaa | agaaaagcat | ttcaggatga | gggaatggca | 1140 |
| tgcgcaaagg | ccctgaggct | gaaatgtgcc | catgtgttct | aagaaatgca | gcgatgctgg | 1200 |
| tgtgcctgga | gcagggacgg | aggggagaa | tgggaggaga | caaggagctg | aaggagtagt | 1260 |
| tcccgaagga | ccttgtgggt | gatatagagg | acttcgcttt | tgctctgagt | gaggtgggag | 1320 |
| ccatagaagc | ttctaagcag | aagagggact | tgccctaatt | caggtgatca | caggtgtctt | 1380 |
| gtggcctcca | tgggaggttg | aaaaccagag | aaggtgaagg | ggggctgcac | tgagccacag | 1440 |
| gaacaatgat | ggagattcca | gctaagccca | gaccccgtgg | attctagata | gattttagag | 1500 |
| gcagcagaca | gaattactga | ggaattgagt | gtaagagtgg | aataaagtta | tcaaggacaa | 1560 |
| tgccaagggt | ggggcacccc | caaatttgac | tctgggagac | tcagccaaat | cctatctggt | 1620 |
| aataaaattt | cttttttatt | tttcttttct | ttctttcttt | ctttttttt | ttttgagtt | 1680 |
| gggatcttgt | gctctgtc | | | | | 1698 |

<210> SEQ ID NO 10
<211> LENGTH: 398
<212> TYPE: PRT
<213> ORGANISM: Homo sapiens
<220> FEATURE:
<221> NAME/KEY: MISC_FEATURE
<223> OTHER INFORMATION: Sphingosine-1-phosphate receptor (SIP) (Figures 14 and 15)

<400> SEQUENCE: 10

```
Met Glu Ser Gly Leu Leu Arg Pro Ala Pro Val Ser Glu Val Ile Val
1               5                   10                  15

Leu His Tyr Asn Tyr Thr Gly Lys Leu Arg Gly Ala Arg Tyr Gln Pro
            20                  25                  30

Gly Ala Gly Leu Arg Ala Asp Ala Val Val Cys Leu Ala Val Cys Ala
        35                  40                  45

Phe Ile Val Leu Glu Asn Leu Ala Val Leu Leu Val Leu Gly Arg His
    50                  55                  60

Pro Arg Phe His Ala Pro Met Phe Leu Leu Leu Gly Ser Leu Thr Leu
65                  70                  75                  80

Ser Asp Leu Leu Ala Gly Ala Ala Tyr Ala Ala Asn Ile Leu Leu Ser
                85                  90                  95

Gly Pro Leu Thr Leu Lys Leu Ser Pro Ala Leu Trp Phe Ala Arg Glu
            100                 105                 110

Gly Gly Val Phe Val Ala Leu Thr Ala Ser Val Leu Ser Leu Leu Ala
        115                 120                 125

Ile Ala Leu Glu Arg Ser Leu Thr Met Ala Arg Arg Gly Pro Ala Pro
    130                 135                 140

Val Ser Ser Arg Gly Arg Thr Leu Ala Met Ala Ala Ala Ala Trp Gly
145                 150                 155                 160

Val Ser Leu Leu Leu Gly Leu Leu Pro Ala Leu Gly Trp Asn Cys Leu
                165                 170                 175

Gly Arg Leu Asp Ala Cys Ser Thr Val Leu Pro Leu Tyr Ala Lys Ala
            180                 185                 190

Tyr Val Leu Phe Cys Val Leu Ala Phe Val Gly Ile Leu Ala Ala Ile
        195                 200                 205

Cys Ala Leu Tyr Ala Arg Ile Tyr Cys Gln Val Arg Ala Asn Ala Arg
    210                 215                 220

Arg Leu Pro Ala Arg Pro Gly Thr Ala Gly Thr Thr Ser Thr Arg Ala
225                 230                 235                 240

Arg Arg Lys Pro Arg Ser Leu Ala Leu Leu Arg Thr Leu Ser Val Val
                245                 250                 255

Leu Leu Ala Phe Val Ala Cys Trp Gly Pro Leu Phe Leu Leu Leu Leu
            260                 265                 270

Leu Asp Val Ala Cys Pro Ala Arg Thr Cys Pro Val Leu Leu Gln Ala
        275                 280                 285

Asp Pro Phe Leu Gly Leu Ala Met Ala Asn Ser Leu Leu Asn Pro Ile
    290                 295                 300

Ile Tyr Thr Leu Thr Asn Arg Asp Leu Arg His Ala Leu Leu Arg Leu
305                 310                 315                 320

Val Cys Cys Gly Arg His Ser Cys Gly Arg Asp Pro Ser Gly Ser Gln
                325                 330                 335

Gln Ser Ala Ser Ala Ala Glu Ala Ser Gly Gly Leu Arg Arg Cys Leu
            340                 345                 350

Pro Pro Gly Leu Asp Gly Ser Phe Ser Gly Ser Glu Arg Ser Ser Pro
        355                 360                 365

Gln Arg Asp Gly Leu Asp Thr Ser Gly Ser Thr Gly Ser Pro Gly Ala
    370                 375                 380

Pro Thr Ala Ala Arg Thr Leu Val Ser Glu Pro Ala Ala Asp
385                 390                 395
```

-continued

```
<210> SEQ ID NO 11
<211> LENGTH: 254
<212> TYPE: PRT
<213> ORGANISM: Homo sapiens
<220> FEATURE:
<221> NAME/KEY: MISC_FEATURE
<223> OTHER INFORMATION: Sphingosine-1-phosphate receptor 1 (SIP1)
      (Figure 14)

<400> SEQUENCE: 11

Met Glu Ser Gly Leu Leu Arg Pro Ala Pro Val Ser Glu Val Ile Val
1               5                   10                  15

Leu His Tyr Asn Tyr Thr Gly Lys Leu Arg Gly Ala Arg Tyr Gln Pro
            20                  25                  30

Gly Ala Gly Leu Arg Ala Asp Ala Val Val Cys Leu Ala Val Cys Ala
        35                  40                  45

Phe Ile Val Leu Glu Asn Leu Ala Val Leu Leu Val Leu Gly Arg His
    50                  55                  60

Pro Arg Phe His Ala Pro Met Phe Leu Leu Leu Gly Ser Leu Thr Leu
65                  70                  75                  80

Ser Val Pro Ala Arg Pro Gly Thr Ala Gly Thr Thr Ser Thr Arg Ala
                85                  90                  95

Arg Arg Lys Pro Arg Ser Leu Ala Leu Leu Arg Thr Leu Ser Val Val
            100                 105                 110

Leu Leu Ala Phe Val Ala Cys Trp Gly Pro Leu Phe Leu Leu Leu Leu
        115                 120                 125

Leu Asp Val Ala Cys Pro Ala Arg Thr Cys Pro Val Leu Leu Gln Ala
    130                 135                 140

Asp Pro Phe Leu Gly Leu Ala Met Ala Asn Ser Leu Leu Asn Pro Ile
145                 150                 155                 160

Ile Tyr Thr Leu Thr Asn Arg Asp Leu Arg His Ala Leu Leu Arg Leu
                165                 170                 175

Val Cys Cys Gly Arg His Ser Cys Gly Arg Asp Pro Ser Gly Ser Gln
            180                 185                 190

Gln Ser Ala Ser Ala Ala Glu Ala Ser Gly Gly Leu Arg Arg Cys Leu
        195                 200                 205

Pro Pro Gly Leu Asp Gly Ser Phe Ser Gly Ser Glu Arg Ser Ser Pro
    210                 215                 220

Gln Arg Asp Gly Leu Asp Thr Ser Gly Ser Thr Gly Ser Pro Gly Ala
225                 230                 235                 240

Pro Thr Ala Ala Arg Thr Leu Val Ser Glu Pro Ala Ala Asp
                245                 250

<210> SEQ ID NO 12
<211> LENGTH: 103
<212> TYPE: PRT
<213> ORGANISM: Homo sapiens
<220> FEATURE:
<221> NAME/KEY: MISC_FEATURE
<223> OTHER INFORMATION: Sphingosine-1-Phosphate receptor 2 (Figure 6)

<400> SEQUENCE: 12

Met Glu Ser Gly Leu Leu Arg Pro Ala Pro Val Ser Glu Val Ile Val
1               5                   10                  15

Leu His Tyr Asn Tyr Thr Gly Lys Leu Arg Gly Ala Arg Tyr Gln Pro
            20                  25                  30

Gly Ala Gly Leu Arg Ala Asp Ala Val Val Cys Leu Ala Val Cys Ala
        35                  40                  45
```

```
Phe Ile Val Leu Glu Asn Leu Ala Val Leu Leu Val Leu Gly Arg His
    50                  55                  60

Pro Arg Phe His Ala Pro Met Phe Leu Leu Leu Gly Ser Leu Thr Leu
 65                  70                  75                  80

Ser Asp Leu Leu Ala Gly Ala Ala Tyr Ala Ala Ala Arg Thr Leu
                85                  90                  95

Val Ser Glu Pro Ala Ala Asp
            100

<210> SEQ ID NO 13
<211> LENGTH: 1245
<212> TYPE: DNA
<213> ORGANISM: Homo sapiens
<220> FEATURE:
<221> NAME/KEY: misc_feature
<223> OTHER INFORMATION: Sphingosine-1-Phosphate receptor 2 (Figure 6)

<400> SEQUENCE: 13
cgcgcggccc atggagtcgg ggctgctgcg gccggcgccg gtgagcgagg tcatcgtcct     60
gcattacaac tacaccggca agctccgcgg tgcgcgctac cagccgggtg ccggcctgcg    120
cgccgacgcc gtggtgtgcc tggcggtgtg cgccttcatc gtgctagaga atctagccgt    180
gttgttggtg ctcggacgcc acccgcgctt ccacgctccc atgttcctgc tcctgggcag    240
cctcacgttg tcggatctgc tggcaggcgc cgcctacgcc gccgccgccc ggactctggt    300
atcagaaccg gctgcagact gacaccctcg gcccacgact gtcttcccaa gttttacaga    360
cttgttcttt ttacataaag gaatttgtag gaaatgcagc caaaggtgca gtcggaaaag    420
atgcagggga aatgtattta tgcagcgaca ccccacaatg tgaacaaaca gacaaaaaat    480
ctgtgccctc gtggaattga cgttctgctt gggaacacag aaaagaactc ggtgatgaaa    540
taatggagat gattccagtg acaaacgaca gagatggtga tggtggtcag ggaagacctc    600
tctgcagagg tagtgacttg tgatgtgagc tgagacctct gtcctgggaa gaccaaaaga    660
aaagcatttc aggatgaggg aatggcatgc gcaaaggccc tgaggctgaa atgtgcccat    720
gtgttctaag aaatgcagcg atgctggtgt gcctggagca gggacggagg gggagaatgg    780
gaggagacaa ggagctgaag gagtagttcc gaaggacct tgtgggtgat atagaggact    840
tcgcttttgc tctgagtgag gtgggagcca tagaagcttc taagcagaag agggacttgc    900
cctaattcag gtgatcacag gtgtcttgtg gcctccatgg gaggttgaaa accagagaag    960
gtgaaggggg gctgcactga gccacaggaa caatgatgga gattccagct aagcccagac   1020
cccgtggatt ctagatagat tttagaggca gcagacagaa ttactgagga attgagtgta   1080
agagtggaat aaagttatca aggacaatgc caagggtggg gcaccccaa atttgactct    1140 gggagactca gccaaatcct atctggtaat aaaatttctt ttttattttt cttttcttc    1200 tttctttctt tttttttttt ttgagttggg atcttgtgct ctgtc                    1245

<210> SEQ ID NO 14
<211> LENGTH: 103
<212> TYPE: PRT
<213> ORGANISM: Homo sapiens
<220> FEATURE:
<221> NAME/KEY: MISC_FEATURE
<223> OTHER INFORMATION: Sphingosine-1-Phosphate receptor 2 (S1P2)
      (Figure 15)

<400> SEQUENCE: 14

Met Glu Ser Gly Leu Leu Arg Pro Ala Pro Val Ser Glu Val Ile Val
 1               5                   10                  15
```

```
Leu His Tyr Asn Tyr Thr Gly Lys Leu Arg Gly Ala Arg Tyr Gln Pro
         20                  25                  30

Gly Ala Gly Leu Arg Ala Asp Ala Val Val Cys Leu Ala Val Cys Ala
             35                  40                  45

Phe Ile Val Leu Glu Asn Leu Ala Val Leu Leu Val Leu Gly Arg His
 50                  55                  60

Pro Arg Phe His Ala Pro Met Phe Leu Leu Leu Gly Ser Leu Thr Leu
 65                  70                  75                  80

Ser Asp Leu Leu Ala Gly Ala Ala Tyr Ala Ala Ala Arg Thr Leu
                 85                  90                  95

Val Ser Glu Pro Ala Ala Asp
             100
```

```
<210> SEQ ID NO 15
<211> LENGTH: 2306
<212> TYPE: DNA
<213> ORGANISM: Homo sapiens
<220> FEATURE:
<221> NAME/KEY: misc_feature
<223> OTHER INFORMATION: Full-length (2.2 kb) nucleotide sequence of
      human S1P5 cDNA (Figure 8)

<400> SEQUENCE: 15
gcgcggccca tggagtcggg gctgctgcgg ccggcgccgg tgagcgaggt catcgtcctg      60
cattacaact acaccggcaa gctccgcggt gcgcgctacc agccgggtgc cggcctgcgc     120
gccgacgccg tggtgtgcct ggcggtgtgc gccttcatcg tgctagagaa tctagccgtg     180
ttgttggtgc tcggacgcca cccgcgcttc cacgctccca tgttcctgct cctgggcagc     240
ctcacgttgt cggatctgct ggcaggcgcc gcctacgccg ccaacatcct actgtcgggg     300
ccgctcacgc tgaaactgtc ccccgcgctc tggttcgcac gggagggagg cgtcttcgtg     360
gcactcactg cgtccgtgct gagcctcctg gccatcgcgc tggagcgcag cctcaccatg     420
gcgcgcaggg ggcccgcgcc cgtctccagt cgggggcgca cgctggcgat ggcagccgcg     480
gcctggggcg tgtcgctgct cctcgggctc ctgccagcgc tgggctggaa ttgcctgggt     540
cgcctggacg cttgctccac tgtcttgccg ctctacgcca aggcctacgt gctcttctgc     600
gtgctcgcct tcgtgggcat cctggccgcg atctgtgcac tctacgcgcg catctactgc     660
caggtacgcg ccaacgcgcg gcgcctgccg gcacggcccg ggactgcggg gaccacctcg     720
acccgggcgc gtcgcaagcc gcgctcgctg gccttgctgc gcacgctcag cgtggtgctc     780
ctggcctttg tggcatgttg gggccccctc ttcctgctgc tgttgctcga cgtggcgtgc     840
ccggcgcgca cctgtcctgt actcctgcag gccgatccct tcctgggact ggccatggcc     900
aactcacttc tgaaccccat catctacacg ctcaccaacc gcgacctgcg ccacgcgctc     960
ctgcgcctgg tctgctgcgg acgccactcc tgcggcagag acccgagtgg ctcccagcag    1020
tcggcgagcg cggctgaggc ttccgggggc ctgcgccgct gcctgccccc gggccttgat    1080
gggagcttca gcggctcgga gcgctcatcg ccccagcgcg acgggctgga caccagcggc    1140
tccacaggca gccccggtgc acccacagcc gcccggactc tggtatcaga accggctgca    1200
gactgacacc ctcggcccac gactgtcttc ccaagtttta cagacttgtt cttttttacat    1260 aaaggaattt gtaggaaatg cagccaaagg tgcagtcgga aaagatgcag gggaaatgta    1320
tttatgcagc gacaccccac aatgtgaaca aacagacaaa aaatctgtgc cctcgtggaa    1380
ttgacgttct gcttgggaac acagaaaaga actcggtgat gaaataatgg agatgattcc    1440
agtgacaaac gacagagatg gtgatggtgg tcagggaaga cctctctgca gaggtagtga    1500
```

```
cttgtgatgt gagctgagac ctctgtcctg ggaagaccaa agaaaagca tttcaggatg    1560 agggaatggc atgcgcaaag gccctgaggc tgaaatgtgc ccatgtgttc taagaaatgc    1620
agcgatgctg gtgtgcctgg agcagggacg agggggaga atgggaggag acaaggagct    1680
gaaggagtag ttcccgaagg accttgtggg tgatatagag gacttcgctt ttgctctgag    1740
tgaggtggga gccatagaag cttctaagca agagggac ttgccctaat tcaggtgatc     1800
acaggtgtct tgtggcctcc atgggaggtt gaaaaccaca gaaggtgaag ggggctgca    1860 ctgagccaca ggaacaatga tggagattcc agctaagccc agaccccgtg gattctagat    1920
agattttaga ggcagcagac agaattactg aggaattgag tgtaagagtg gaataaagtt    1980
atcaaggaca atgccaaggg tggggcaccc ccaaatttga ctttgggaga ctcagccaaa    2040
tcctatctgg taataaaatt tcttttttat ttttcttttc tttctttctt tctttctttc    2100
tttttttttt tttgagttgg gatcttgtgc tctgtcaccc aggctggagt gcaatgggca    2160
caattatagc tcactgcagc ctggaactcc tgggatcaag cctggagttc ctgcttcagc    2220
ctccctagta gctgggacta caggcatgca ccaccatgcc cagttaataa aatttcttca    2280
aatgcaaaaa aaaaaaaaaa aaaaaa                                         2306

<210> SEQ ID NO 16
<211> LENGTH: 398
<212> TYPE: PRT
<213> ORGANISM: Homo sapiens
<220> FEATURE:
<221> NAME/KEY: MISC_FEATURE
<223> OTHER INFORMATION: Deduced amino acid sequence of human S1P5 cDNA
      coding region (Figure 8)

<400> SEQUENCE: 16

Met Glu Ser Gly Leu Leu Arg Pro Ala Pro Val Ser Glu Val Ile Val
1               5                   10                  15

Leu His Tyr Asn Tyr Thr Gly Lys Leu Arg Gly Ala Arg Tyr Gln Pro
            20                  25                  30

Gly Ala Gly Leu Arg Ala Asp Ala Val Val Cys Leu Ala Val Cys Ala
        35                  40                  45

Phe Ile Val Leu Glu Asn Leu Ala Val Leu Leu Val Leu Gly Arg His
    50                  55                  60

Pro Arg Phe His Ala Pro Met Phe Leu Leu Leu Gly Ser Leu Thr Leu
65                  70                  75                  80

Ser Asp Leu Leu Ala Gly Ala Ala Tyr Ala Ala Asn Ile Leu Leu Ser
                85                  90                  95

Gly Pro Leu Thr Leu Lys Leu Ser Pro Ala Leu Trp Phe Ala Arg Glu
            100                 105                 110

Gly Gly Val Phe Val Ala Leu Thr Ala Ser Val Leu Ser Leu Leu Ala
        115                 120                 125

Ile Ala Leu Glu Arg Ser Leu Thr Met Ala Arg Arg Gly Pro Ala Pro
    130                 135                 140

Val Ser Ser Arg Gly Arg Thr Leu Ala Met Ala Ala Ala Trp Gly
145                 150                 155                 160

Val Ser Leu Leu Leu Gly Leu Leu Pro Ala Leu Gly Trp Asn Cys Leu
                165                 170                 175

Gly Arg Leu Asp Ala Cys Ser Thr Val Leu Pro Leu Tyr Ala Lys Ala
            180                 185                 190

Tyr Val Leu Phe Cys Val Leu Ala Phe Val Gly Ile Leu Ala Ala Ile
        195                 200                 205

Cys Ala Leu Tyr Ala Arg Ile Tyr Cys Gln Val Arg Ala Asn Ala Arg
```

```
            210                 215                 220
Arg Leu Pro Ala Arg Pro Gly Thr Ala Gly Thr Thr Ser Thr Arg Ala
225                 230                 235                 240

Arg Arg Lys Pro Arg Ser Leu Ala Leu Leu Arg Thr Leu Ser Val Val
                245                 250                 255

Leu Leu Ala Phe Val Ala Cys Trp Gly Pro Leu Phe Leu Leu Leu Leu
                260                 265                 270

Leu Asp Val Ala Cys Pro Ala Arg Thr Cys Pro Val Leu Leu Gln Ala
                275                 280                 285

Asp Pro Phe Leu Gly Leu Ala Met Ala Asn Ser Leu Leu Asn Pro Ile
                290                 295                 300

Ile Tyr Thr Leu Thr Asn Arg Asp Leu Arg His Ala Leu Leu Arg Leu
305                 310                 315                 320

Val Cys Cys Gly Arg His Ser Cys Gly Arg Asp Pro Ser Gly Ser Gln
                325                 330                 335

Gln Ser Ala Ser Ala Ala Glu Ala Ser Gly Gly Leu Arg Arg Cys Leu
                340                 345                 350

Pro Pro Gly Leu Asp Gly Ser Phe Ser Gly Ser Glu Arg Ser Ser Pro
                355                 360                 365

Gln Arg Asp Gly Leu Asp Thr Ser Gly Ser Thr Gly Ser Pro Gly Ala
370                 375                 380

Pro Thr Ala Ala Arg Thr Leu Val Ser Glu Pro Ala Ala Asp
385                 390                 395

<210> SEQ ID NO 17
<211> LENGTH: 398
<212> TYPE: PRT
<213> ORGANISM: Homo sapiens
<220> FEATURE:
<221> NAME/KEY: MISC_FEATURE
<223> OTHER INFORMATION: Predicted amino acid sequence of S1P5 (Figures
      12A and 12B)

<400> SEQUENCE: 17

Met Glu Ser Gly Leu Leu Arg Pro Ala Pro Val Ser Glu Val Ile Val
1               5                   10                  15

Leu His Tyr Asn Tyr Thr Gly Lys Leu Arg Gly Ala Arg Tyr Gln Pro
                20                  25                  30

Gly Ala Gly Leu Arg Ala Asp Ala Val Val Cys Leu Ala Val Cys Ala
                35                  40                  45

Phe Ile Val Leu Glu Asn Leu Ala Val Leu Leu Val Leu Gly Arg His
                50                  55                  60

Pro Arg Phe His Ala Pro Met Phe Leu Leu Leu Gly Ser Leu Thr Leu
65                  70                  75                  80

Ser Asp Leu Leu Ala Gly Ala Ala Tyr Ala Ala Asn Ile Leu Leu Ser
                85                  90                  95

Gly Pro Leu Thr Leu Lys Leu Ser Pro Ala Leu Trp Phe Ala Arg Glu
                100                 105                 110

Gly Gly Val Phe Val Ala Leu Thr Ala Ser Val Leu Ser Leu Leu Ala
                115                 120                 125

Ile Ala Leu Glu Arg Ser Leu Thr Met Ala Arg Arg Gly Pro Ala Pro
                130                 135                 140

Val Ser Ser Arg Gly Arg Thr Leu Ala Met Ala Ala Ala Ala Trp Gly
145                 150                 155                 160

Val Ser Leu Leu Leu Gly Leu Leu Pro Ala Leu Gly Trp Asn Cys Leu
                165                 170                 175
```

-continued

```
Gly Arg Leu Asp Ala Cys Ser Thr Val Leu Pro Leu Tyr Ala Lys Ala
            180                 185                 190

Tyr Val Leu Phe Cys Val Leu Ala Phe Val Gly Ile Leu Ala Ala Ile
        195                 200                 205

Cys Ala Leu Tyr Ala Arg Ile Tyr Cys Gln Val Arg Ala Asn Ala Arg
    210                 215                 220

Arg Leu Pro Ala Arg Pro Gly Thr Ala Gly Thr Thr Ser Thr Arg Ala
225                 230                 235                 240

Arg Arg Lys Pro Arg Ser Leu Ala Leu Leu Arg Thr Leu Ser Val Val
                245                 250                 255

Leu Leu Ala Phe Val Ala Cys Trp Gly Pro Leu Phe Leu Leu Leu Leu
            260                 265                 270

Leu Asp Val Ala Cys Pro Ala Arg Thr Cys Pro Val Leu Leu Gln Ala
        275                 280                 285

Asp Pro Phe Leu Gly Leu Ala Met Ala Asn Ser Leu Leu Asn Pro Ile
    290                 295                 300

Ile Tyr Thr Leu Thr Asn Arg Asp Leu Arg His Ala Leu Leu Arg Leu
305                 310                 315                 320

Val Cys Cys Gly Arg His Ser Cys Gly Arg Asp Pro Ser Gly Ser Gln
                325                 330                 335

Gln Ser Ala Ser Ala Ala Glu Ala Ser Gly Gly Leu Arg Arg Cys Leu
            340                 345                 350

Pro Pro Gly Leu Asp Gly Ser Phe Ser Gly Ser Glu Arg Ser Ser Pro
        355                 360                 365

Gln Arg Asp Gly Leu Asp Thr Ser Gly Ser Thr Gly Ser Pro Gly Ala
    370                 375                 380

Pro Thr Ala Ala Arg Thr Leu Val Ser Glu Pro Ala Ala Asp
385                 390                 395

<210> SEQ ID NO 18
<211> LENGTH: 254
<212> TYPE: PRT
<213> ORGANISM: Homo sapiens
<220> FEATURE:
<221> NAME/KEY: MISC_FEATURE
<223> OTHER INFORMATION: Predicted amino acid sequence of S1P5-alpha
      (Figure 12A)

<400> SEQUENCE: 18

Met Glu Ser Gly Leu Leu Arg Pro Ala Pro Val Ser Glu Val Ile Val
1               5                   10                  15

Leu His Tyr Asn Tyr Thr Gly Lys Leu Arg Gly Ala Arg Tyr Gln Pro
            20                  25                  30

Gly Ala Gly Leu Arg Ala Asp Ala Val Val Cys Leu Ala Val Cys Ala
        35                  40                  45

Phe Ile Val Leu Glu Asn Leu Ala Val Leu Leu Val Leu Gly Arg His
    50                  55                  60

Pro Arg Phe His Ala Pro Met Phe Leu Leu Leu Gly Ser Leu Thr Leu
65                  70                  75                  80

Ser Val Pro Ala Arg Pro Gly Thr Ala Gly Thr Thr Ser Thr Arg Ala
                85                  90                  95

Arg Arg Lys Pro Arg Ser Leu Ala Leu Leu Arg Thr Leu Ser Val Val
            100                 105                 110

Leu Leu Ala Phe Val Ala Cys Trp Gly Pro Leu Phe Leu Leu Leu Leu
        115                 120                 125

Leu Asp Val Ala Cys Pro Ala Arg Thr Cys Pro Val Leu Leu Gln Ala
    130                 135                 140
```

```
Asp Pro Phe Leu Gly Leu Ala Met Ala Asn Ser Leu Leu Asn Pro Ile
145                 150                 155                 160

Ile Tyr Thr Leu Thr Asn Arg Asp Leu Arg His Ala Leu Leu Arg Leu
                165                 170                 175

Val Cys Cys Gly Arg His Ser Cys Gly Arg Asp Pro Ser Gly Ser Gln
            180                 185                 190

Gln Ser Ala Ser Ala Ala Glu Ala Ser Gly Gly Leu Arg Arg Cys Leu
        195                 200                 205

Pro Pro Gly Leu Asp Gly Ser Phe Ser Gly Ser Glu Arg Ser Ser Pro
    210                 215                 220

Gln Arg Asp Gly Leu Asp Thr Ser Gly Ser Thr Gly Ser Pro Gly Ala
225                 230                 235                 240

Pro Thr Ala Ala Arg Thr Leu Val Ser Glu Pro Ala Ala Asp
                245                 250

<210> SEQ ID NO 19
<211> LENGTH: 103
<212> TYPE: PRT
<213> ORGANISM: Homo sapiens
<220> FEATURE:
<221> NAME/KEY: MISC_FEATURE
<223> OTHER INFORMATION: Predicted amino acid sequence of S1P5-beta
      (Figure 12B)

<400> SEQUENCE: 19

Met Glu Ser Gly Leu Leu Arg Pro Ala Pro Val Ser Glu Val Ile Val
1               5                   10                  15

Leu His Tyr Asn Tyr Thr Gly Lys Leu Arg Gly Ala Arg Tyr Gln Pro
            20                  25                  30

Gly Ala Gly Leu Arg Ala Asp Ala Val Val Cys Leu Ala Val Cys Ala
        35                  40                  45

Phe Ile Val Leu Glu Asn Leu Ala Val Leu Val Leu Gly Arg His
    50                  55                  60

Pro Arg Phe His Ala Pro Met Phe Leu Leu Leu Gly Ser Leu Thr Leu
65                  70                  75                  80

Ser Asp Leu Leu Ala Gly Ala Ala Tyr Ala Ala Ala Ala Arg Thr Leu
            85                  90                  95

Val Ser Glu Pro Ala Ala Asp
            100
```

SPHINGOSINE 1-PHOSPHATE RECEPTOR GENE, SPPR

CROSS REFERENCE TO RELATED APPLICATIONS

The present application is a continuation of U.S. application Ser. No. 12/193,428, filed Aug. 18, 2008, which is a continuation of U.S. application Ser. No. 11/653,811, filed Jan. 16, 2007, now abandoned, which is a continuation of U.S. application Ser. No. 10/024,019, filed Dec. 21, 2001, now U.S. Pat. No. 7,220,580, which claims benefit of U.S. Provisional Application Ser. No. 60/257,119, filed Dec. 22, 2000, each of which is hereby incorporated by reference herein in its entirety, including any figures, tables, nucleic acid sequences, amino acid sequences, and drawings.

FIELD OF THE INVENTION

The present invention relates to the genetics of autoimmune diseases, including lymphoproliferative diseases, such as large granular lymphocyte leukemia (LGL), and rheumatoid arthritis (RA). Specifically, the invention relates to a novel sphingosine 1-phosphate receptor gene, herein termed sppr, and its splice variants. Sppr is up-regulated in LGL and is useful, for example, in the diagnosis and treatment of certain lymphoproliferative, neurodegenerative and autoimmune diseases.

BACKGROUND OF THE INVENTION

Large granular lymphocyte leukemia (LGL) is a rare form of lymphoproliferative disorder often associated with autoimmune disease (Loughran T. P., Clonal diseases of large granular lymphocytes. Blood 82, 1-14, 1993).

The cause of LGL is still not hilly understood. An increased count of large granular lymphocytes is characteristic of LGL leukemia. Patients with clonal CD3+LGL, as determined by cytogenetic or T-cell receptor (TCR) gene rearrangement studies, are classified as T-LGL. Some of these patients may resemble those with Felty's syndrome with clinical features of rheumatoid arthritis, neutropenia and splenomegaly (Ahem M. J., et al., P. Phenotypic and genotypic analysis of mononuclear cells from patients with Felty's syndrome. Ann. Rheum. 49, 103-108, 1990.) Morbidity and mortality in patients with LGL leukemia typically results from infections acquired during severe neutropenia.

The etiology of LGL leukemia is also not yet known. There is strong evidence that suggests that leukemic large granular lymphocytes are antigen activated cytotoxic T lymphocytes (CTL), but the nature of the antigen and of the initial stimulus leading to antigen driven expansion are not known.

LGL leukemic cells express FAS and FAS ligand, but they are not actively undergoing apoptosis (Perzova, R and Loughran, T. P, Jr. Constitutive expression of Fas ligand in large granular lymphocyte leukemia. British Jnl. Haematology, 1997). How they acquire resistance to apoptosis is not known.

Within the field of the diagnosis and treatment of LGL and other autoimmune diseases, there is a need for better tools for diagnosis and early detection of disease, specific therapeutic targets and treatments for the disease, and more specific reagents and tools with which to identify the pathogenic pathways of these diseases. The present invention provides a novel gene and splice variants that are linked to these diseases, and which address the aforementioned needs and more, as will become clear to one of skill in the art upon reading the following disclosure.

SUMMARY OF THE INVENTION

Large granular lymphocyte leukemia (LGL) is a lymphoproliferative disorder often associated with autoimmune disease. In order to identify differentially expressed genes in LGL leukemia, microarray analysis is performed from RNA isolated from PBMC of LGL leukemia patients and compared with normal healthy individual(s). By screening a human LGL leukemia library the full-length sequence of a human gene that showed 85% identity with rat sphingosine 1-phosphate receptor is obtained. Two different isoforms are also identified by RT-PCR, designated sphingosine 1-phosphate receptor 1, also referred to as S1p5-α and sphingosine 1-phosphate receptor 2, also referred to as S1P5-β. Sphingosine 1-phosphate receptor (sppr) is present in brain, spleen, PBMCs, liver and kidney. The present inventors found it is over-expressed in LGL leukemia patients when compare to normal individuals.

In a first embodiment, the invention provides a gene comprising sppr or a splice 5 variant, or sppr protein or modified proteins or fragments thereof.

In a further embodiment, the invention provides a nucleic acid capable of hybridizing to at least a portion of said sppr gene, including splice variants.

In a further embodiment, the invention provides methods for screening for autoimmune diseases, including LGL or rheumatoid arthritis, based on overexpression of sppr.

In a further embodiment, the invention provides for monoclonal antibodies to sppr and their use in detection, diagnosis and treatment of disease states.

In a further embodiment, the invention provides for screening of ligands, agonists, and antagonists of sppr.

In a further embodiment, the invention provides for inhibition or treatment of neurodegenerative disease.

In a preferred embodiment the present invention provides a sphingosine 1-phosphate receptor gene. The use of said gene makes it possible to produce the sphingosine 1-phosphate receptor protein with ease and in large quantities, and said protein, which has sphingosine 1-phosphate receptor activity, can be used in developing therapeutic agents for various diseases.

Throughout this document the nomenclature sppr and S1P5 are used interchangeably. The receptor was initially termed sppr. However, to be consistent with a new nomenclature system this receptor was renamed S1P5.

DESCRIPTION OF THE FIGURES

FIG. 1A-B illustrates a microarray of the differential expression of the selected EST. (EST (GenBank ID 1868427) is obtained Incyte Genomics.) FIG. 1A-B shows a microarray hybridized with the fluorescent labeled probes generated using mRNA isolated from PBMC of LGL leukemia patient and from mRNA isolated from normal healthy individual. FIG. 1A illustrates a microarray showing the expression of an LGL leukemia patient cDNAs. FIG. 1B illustrates a microarray showing the expression of a normal healthy individual. Arrows show the expression of EST in both patient and normal individual (GeneBank Id: N47089). Intensity bar shows the increased expression starting from left to right. A balanced differential expression of 3.0 is determined for this EST.

FIG. 3 shows the complete nucleotide sequence, SEQ ID NO: 4, of human sphingosine 1-Phosphate receptor (SPPR) cDNA and amino acid sequence (SEQ ID NO: 3) as predicted by the nucleic acid sequence. The full-length (2.2 kb) nucleotide sequence of sppr is compiled from sequences of clones isolated from an LGL leukemia library and RT-PCR products obtained by using the gene specific primers designed using the corresponding sequence from chromosome 19.

FIG. 4 shows the alignment of the amino acid sequence of SPPR with other members of the sphingosine 1-phosphate receptor family. The deduced amino acid sequence of sppr is compared with rat edg-1 and nrg-1. There is approximately 85% identity with these genes.

FIG. 5 shows the nucleotide sequence and deduced amino acid sequence of splice variant, sphingosine 1-phosphate receptor 1. 1.6 kb fragment is obtained by RT-PCR using total RNA isolated from PBMC of an LGL leukemia patient. The fragment is then cloned and sequenced.

FIG. 6 shows the nucleotide sequence and deduced amino acid sequence of splice variant, sphingosine 1-phosphate receptor 2. The nucleotide sequence of an alternative splice variant of sppr and deduced sequence. 1.2 kb fragment is obtained from RT-PCR using total RNA isolated from PBMC of LGL leukemia. The fragment is then cloned and sequenced.

FIG. 8 shows nucleotide and deduced amino acid sequence of human $S1P_5$ cDNA. Full-length (2.2 kb) nucleotide sequence of $S1P_5$ is compiled from the sequences of clones isolated from LGL leukemia library (clone 6) and RT-PCR products. GenBank Accession No. AF331840. The predicted amino acids of the coding region are shown underneath by a single letter abbreviation. The left side of the sequence shows nucleotide numbers and the right side shows amino acid numbers. Possible seven transmembrane helices are underlined. The putative polyadenylation sites are in bold.

FIG. 9 shows Alignment of the deduced amino acid sequence of $S1P_5$ with other members: The deduced amino acid sequence of $S1P_5$ is compared with predicted amino acid sequences of rat edg-8 and nrg-1. There is approximately 86% identity with these genes. *—single, fully conserved residue, :—conservation of strong groups, .—conservation of weak groups, —no consensus.

FIG. 10A illustrates a representative autoradiogram of $^{32}P$ incorporation into MBP catalyzed by HA-ERK 2 immunoprecipitated from transiently transfected cells treated as indicated. FIG. 10B illustrates the corresponding Western blot demonstrating the amount of HA-ERK2 present in each of the immune complexes. FIG. 10C illustrates a plot of ERK 2 activity (fold) normalized to the amount of ERK2 protein (means±SD from three independent experiments).

FIG. 12A-B shows comparison of the predicted amino acid sequences of $S1P_5$, $S1P_5$-α and $S1P_5$-β. The predicted amino acid sequences are aligned using CLUSTAL program. FIG. 12A illustrates the nucleotide sequence of an alternative splice variant of $S1P_5$-α and deduced amino acid sequence. A 1.6 kb fragment is obtained from RT-PCR using total RNA isolated from PBMC of LGL leukemia patient. This fragment is cloned and sequenced. FIG. 12B illustrates the nucleotide sequence of an alternative splice variant of $S1P_5$-β and deduced sequence. A 1.2 kb fragment is obtained from RT-PCR using total RNA isolated from PBMC of LGL leukemia. This fragment is cloned and sequenced.

DETAILED DESCRIPTION OF THE INVENTION

Figure 2:
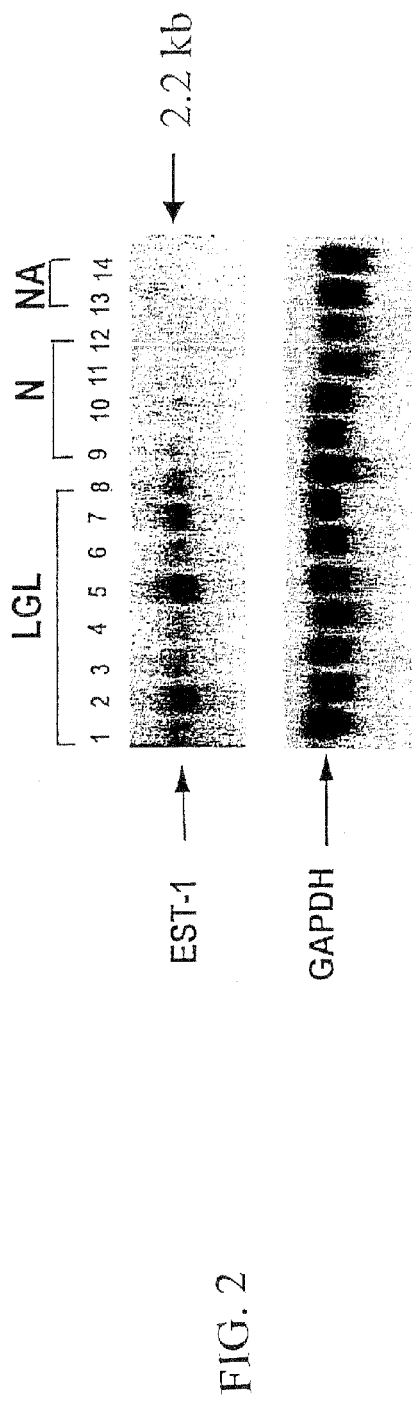
FIG. 2 shows Northern blot analysis performed with 10 ug of total RNA isolated from PBMC of LGL leukemia patients and normal healthy individuals. These results demonstrate over-expression of EST in the PBMCs of LGL leukemia when compared to normal and normal activated PBMCs of healthy individuals.

The abbreviations for amino acids, peptides, base sequences, nucleic acids and so forth as used herein in the present specification are those recommended by the International Union of Pure and Applied Chemistry (IUPAC) and the International Union of Biochemistry (IUB) and in the "Guidelines for drafting patent specifications relative to base sequences and/or amino acid sequences" edited by the Japanese Patent Office or those commonly used in the relevant field of art.

Although the genes of the present invention is represented by a single-stranded DNA sequence, as shown under, for example, SEQ ID NO:4, the present invention also includes the DNA sequence complementary to such a single-stranded DNA sequence as well as a component comprising both of these. The DNA sequence representing the gene of the present invention shown in the above-mentioned SEQ ID NO: 4 is an example of the codon combination coding for the respective amino acid residues according to the amino acid sequence shown in SEQ ID NO:7. The gene of the present invention is not limited to the above-mentioned one but may, of course, have any other DNA base sequence comprising a combination of codons arbitrarily selected for the respective amino acid residues without altering the above-mentioned amino acid sequence. Selection of said codons can be carried out by the conventional method in which the codon usage or codon choice in the host to be used for gene recombination is taken into consideration [Nucl. Acids Res., 9, 43-74 (1981)], and these codons can be produced, for example by chemical synthesis, etc.

The gene of the present invention further includes DNA sequences coding for those equivalents to the above-mentioned amino acid sequence that are derived from the latter by deletion, addition or like modification of one or more amino acid residues or part of the amino acid sequence and have similar sphingosine 1-phosphate receptor activity to that of the sphingosine 1-phosphate receptor protein. While production, alteration (mutation) or the like of these polypeptides may occur spontaneously, they can also be produced by post-translational modification. Furthermore, any desired gene can be produced by gene engineering techniques such as the site-specific mutagenesis technique in which the natural gene (gene of the present invention) is altered, by a chemical synthesis technique such as the phosphite triester method in which mutant DNAs are synthesized or by combining both procedures. By utilizing the gene of the present invention, namely by incorporating the same into a vector for use with a microorganism, for instance, and cultivating the transformant microorganism, the sphingosine 1-phosphate receptor protein can be expressed readily and in large quantities, and said protein can be isolated and provided. Since said protein has sphingosine 1-phosphate receptor activity, it is effective for various pharmacological purposes, and it is also useful, among others, in elucidating the pathogenesis, the pathologies or the like of various diseases. More specifically, the recombinant sphingosine 1-phosphate receptor protein obtained by utilizing the gene of the present invention can effectively be used, for example, in elucidating the mechanism of immunosuppression in living bodies, developing or screening out therapeutic agents for autoimmune diseases (e.g. rheumatism, SLE (systemic lupus erythematodes), LGL, etc.), searching for endogenous ligands and substrates to the novel protein and developing therapeutic agents therefor.

Similarly, the gene of the present invention can effectively be used, for example, in elucidating the mechanism of neurodegeneration in living bodies, developing or screening out therapeutic agents for neurodegenerative diseases (e.g. alzheimers, parkinson's and the like), searching for endogenous ligands and substrates to the novel protein and developing therapeutic agents therefor.

In the following, the gene of the present invention will be described in more detail. The gene of the present invention can be isolated by general genetic engineering techniques, for example, by selecting an appropriate clone from among a human fetal brain cDNA library (cDNA synthesized in the conventional manner from mRNA isolated and purified from total RNA obtained in turn from appropriate origin cells containing a gene coding for the sphingosine 1-phosphate receptor protein) using appropriate probes, such as for example those of SEQ ID 1 and SEQ ID2, purifying said clone, and determining the base sequence thereof. In the above procedure, the origin cells may be any animal cells or tissues where the occurrence of sphingosine 1-phosphate receptor protein is known (see for example, the experiment producing the results shown in FIG. 6), or soluble fractions of cultured cells derived therefrom. This can be isolated and purified for the culture supernatant by various chromatographic processes.

In the practice of the present invention, it is also possible to use a part of the DNA fragment sequenced in the above manner as a probe, label this using a random prime DNA labeling kit (available from Takara Shuzo, Amersham, etc.) in accordance with the random prime DNA labeling method (Feinberg, A. P., et al., Anal. Biochem., 137, 266-267 (1984)), for instance, and use the thus-obtained labeled probe in screening out the desired sphingosine 1-phosphate receptor protein gene.

Using the above-mentioned labeled probe, for instance, the desired DNA can be screened out by the plaque hybridization technique developed by Benton and Davis (Benton, W. and Davis, R., Science, 196, 383-394 (1977)).

The gene of the present invention as obtained in the above manner can be cloned in various plasmids in the conventional manner. For instance, after cleavage with an appropriate restriction enzyme and purification, the gene of the present invention can be inserted into a cloning vector (e.g. plasmid) cleaved with the same restriction enzyme and purified, at the cleavage site thereof, whereby a recombinant plasmid can be obtained. By introducing said recombinant into an appropriate host (e.g. *Escherichia coli*) for transformation, a restriction enzyme map of the clone containing said gene can be drawn using the transformant by a conventional known method, for example the method as described in Sambrook, J. Fritsch, E. F., and Maniatis. Molecular cloning. A laboratory Manual 2nd edition. Cold Spring Harbor laboratory Press. Cold Spring Harbor, N.Y. After digestion of the above clone with an appropriate restriction enzyme, the base sequence of said clone can be determined by the above-mentioned dideoxy method or the Maxam-Gilbert method, for instance. The base sequence determination mentioned above may also be readily performed using a commercially available kit or the like.

The thus-determined DNA base sequence of the sphingosine 1-phosphate receptor protein gene of the present invention and the corresponding amino acid sequence encoded thereby are as shown in the sequence listing under SEQ ID NO: 3 and SEQ ID NO:4.

Using the above-mentioned gene (DNA) of the present invention, the recombinant sphingosine 1-phosphate receptor protein can be obtained by various known gene recombination techniques [cf. for example Science, 224, 1431 (1984); Biochem. Biophys. Res. Comm., 130, 692 (1985); Proc. Natl. Acad. Sci. USA, 80, 5990 (1983)]. Said sphingosine 1-phosphate receptor protein is produced, in more detail, by constructing a recombinant DNA allowing expression of the gene of the present invention in host cells, introducing this into host cells for transformation thereof, and cultivating the transformant strain. The host cells may be either eukaryotic or prokaryotic. As an expression vector for use with vertebrate cells, it is possible to use one containing a promoter generally located upstream of the gene to be expressed, an RNA splicing site, a polyadenylation site and a transcription termination sequence and so on. This may further have a replication origin, as necessary. Yeasts are often and generally used as eukaryotic microorganisms and, among them, yeasts belonging to the genus *Saccharomyces* are advantageously used. Usable as expression vectors for use with said yeasts and other eukaryotic microorganisms are pAM82 (A. Miyanohara et al., Proc. Natl. Acad. Sci. USA, 80, 1-5 (1983)) containing a promoter for the acid phosphatase gene, and like vectors. *Escherichia coli* and *Bacilus subtilis* are generally and very often used as prokaryotic host cells. When these are used as hosts in the practice of the present invention, an expression plasmid is preferably used which is derived, for instance, from a plasmid vector capable of replication in said host microorganisms and provided with a promoter, the SD (Shine and Dalgarno) base sequence and further an initiation codon (e.g. ATG) necessary for the initiation of protein synthesis, upstream from the gene of the present invention so that said gene can be expressed. As the host *Escherichia coli* mentioned above, the strain *Escherichia coli* K12 and the like are often used and, as the vector, pBR322 is generally and often used. However, the host and vector are not limited thereto, but other various known microbial strains and vectors can also be used. As regards the promoter, the tryptophan (trp) promoter, 1 pp promoter, lac promoter and P.sub.L promoter, for instance, can be used.

The thus-obtained desired recombinant DNA can be introduced into host cells for transformation thereof by various conventional methods. The transformant obtained can be cultivated in the conventional manner, leading to production and accumulation of the desired sphingosine 1-phosphate receptor protein encoded by the gene of the present invention. The medium to be used in said cultivation can adequately be selected, according to the host cells employed, from among various media in common use. When *Escherichia coli* or like cells are used as host cells, for instance, transformant cultivation can be conducted using LB medium, E medium, M9 medium, M63 medium or the like. To these media, there may be added, as necessary, generally known various carbon sources, nitrogen sources, inorganic salts, vitamins, nature-derived extracts, physiologically active substances, etc. The above-mentioned transformant cultivation can be carried out under conditions suited for the growth of the host cells. In the case of *Escherichia coli*, such conditions can be employed, for instance, as a pH of about 5 to 8, preferably 7 or thereabout, and a temperature of about 20 to 43.degree. C., preferably 37.degree. C. or thereabout. In the above manner, the transformant cells produce and accumulate intracellularly or secrete extracellularly the desired recombinant FK506 binding protein.

Said desired protein can be isolated and purified by various separation techniques utilizing its physical, chemical and other properties [cf. for example "Seikagaku (Biochemistry) Data Book II", pages 1175-1259, 1st edition, 1st printing, published Jun. 23, 1980 by Kabushiki Kaisha Tokyo Kagaku Dojin; Biochemistry, vol. 25, No. 25, 8274-8277 (1986); Eur. J. Biochem., 163, 313-321 (1987)]. As specific examples of said techniques, there may be mentioned conventional reconstitution treatment, treatment with a protein precipitating agent (salting out), centrifugation, osmotic pressure shock treatment, ultrasonic disruption, ultrafiltration, various liquid chromatographic processes such as molecular sieve chromatography (gel filtration), adsorption chromatography, ion exchange chromatography, affinity chromatography and high performance liquid chromatography (HPLC), dialysis, and combinations of these. In the above manner, the desired recombinant protein can be produced on an industrial scale with ease and with high efficiency.

In order to provide diagnostics for LGL leukemia, and provide therapeutic targets for drugs directed to mitigate the pathogenesis of LGL leukemia, microarray analysis is performed to identify differentially expressed genes. A large number of genes are identified that are differentially expressed in LGL leukemia compared to normal controls. One of the ESTs of approximately 300 base pairs is fully characterized herein. Initial Blast analysis shows 100% homology with Homo-sapiens full-length insert cDNA clone YY 85D04 (gb/AF 088014). No open reading frame within the full-length insert cDNA. Therefore, in order get the complete sequence of the gene, the LGL leukemia library is screened and also RT-PCR is performed using the total RNA isolated from different LGL leukemia patients. 15 positive clones are selected from library screening. All of them give partial sequences with the longest one being approximately 340 base pairs shorter (clone 6). BLAST search with htgs, shows that clone 6 shows 100% homology with genomic sequence present in the chromosome 19. Primers are designed based on the genomic sequence information to obtain full-length sequence of the gene. By using these primers in the PCR with genomic DNA and RT-PCR with total RNA, the full-length gene, SEQ ID:4 is obtained. This gene belongs to the G-protein-coupled receptor super-family of integral membrane proteins. BLAST analysis of the complete gene reveals 85% homology with rat sphingosine 1-phosphate receptor edg-8 and nrg-1 (Im, D., et al., Characterization of a Novel sphingosine 1-Phosphate receptor, Edg-8. J. Biol. Chem. 275. 1428 1-14286 (2000); Glickman, M., et al., Molecular cloning, tissue-specific expression and chromosomal localization of a novel nerve growth factor regulated G-protein-coupled receptor, nrg-1. Mol. Cell. Neurosci. 14, 141-152 (1999)), shown in FIG. 4. It is interesting to note that this gene is present mainly in brain, spleen and PBMCs (FIG. 7), and it is over expressed in PBMC of LGL leukemia patients and is be involved in LGL leukemia cell survival or proliferation.

Material and Methods:

Isolation of Peripheral blood mononuclear cells (PBMC and RNA). PBMC are isolated from normal healthy individuals and from LGL leukemia patients. Trizole is obtained from GTBCO-BRL. EST (GenBank ID 1868427) is obtained Incyte Genomics. Oligotex mRNA mini-kit, plasmid isolation kits, gel extraction kits, and PCR reagents are purchased from Qiagen; RNA loading dye is from Sigma Chemical Co. The Prime-a-Gene labeling kit is from Promega Corp. (Madison, Wis.). Deoxycytidine 5' triphosphate dCTP a-32P (3,000 Ci/mmol) is from Dupont NEN (Boston, Mass.). Nytran membrane is obtained from Schleicher & Schuell, Inc., 10 optical Avenue, Keene, N. H. Nick translation columns are obtained from Pharmacia Chemical Co. The Topo-TA cloning kit is from Invitrigen.

PBMC are isolated from whole blood using Ficoll-Hypaque density gradient centrifugation. The PBMC cells are suspended in Trizole reagent (GIBCO-BRL, Rockville. Md.) and total RNA is immediately isolated according to the Oligotex mRNA mini-kit manufacturer's instructions and stored at −70° C. Poly A+ RNA is isolated from total RNA by using Oliogo-Tex mini mRNA kit according to the manufacturer's recommendations. PBMCs are cultured in vitro and activated by Interleukin 2 and phytohemagglutinin (PHA) for 2 to 3 days. In a preferred embodiment, PBMC is cultured in vitro and activated by PHA, (Sigma Chemical Co. St. Louis, Mo.) (1 μg/ml, 2 days) and Interleukin-2 (IL-2) (100 U/ml, 10 days), Next, total RNA is isolated as described above.

Microarray probing and analysis is done by Incyte Genomics, (St. Louis, Mo.). Approximately 1 ug of Poly (A)$^+$ RNA isolated from PBMCs of LGL leukemia and healthy individual is reverse transcribed to generate Cys3 and Cys 5 fluorescently labeled cDNA probes. In a preferred embodiment, more than 90% of PBMC from the LGL leukemia patient are leukemic LGL as indicated by CD 8$^+$ staining. cDNA probes are competitively hybridized to a human Uni-GEM V cDNA microarray containing approximately 7075 immobilized cDNA fragments (4107 known genes and 2968 ESTs). Scanning and quantitation is performed by Incyte Genomics and balanced differential differentiation is given for all the genes. The balanced differential expression is calculated using the ratio between the P1 signal (intensity reading for probe 1) and the balanced P2 signal (intensity reading for probe 2 adjusted using the balanced coefficient). A balanced differential expression of 2.0 is considered indicative of up-regulation of a given gene.

Verification of clones: GEM cDNA clones are purchased from Incyte Genomics as individual bacterial stabs and streaked on LB/agar plates containing appropriate antibiotic(s). Individual colonies are picked and grown in LB medium. Plasmid DNA is isolated and sequenced in order to verify the correct identity of each clone.

Northern Blot analysis: Northern Blotting is done as described previously (Sambrook et al, 1998). Essentially, 10 ug of total RNA from each sample is denatured at 65° C. in a RNA loading buffer, electrophoresed in 1% agarose containing 2.2 M formaldehyde gel, and blotted onto a Nytran membrane. (Nytran membrane obtained from Schleicher & Schuell, Inc, Keene, N.H). The RNA is fixed to the membrane by UV cross-linking. cDNA is labeled with [$^{32}$P] (Prime-a-Gene labeling kit from Promega Corp. Madison, Wis., deoxycytidine 5' triphosphate (dCTP α-$^{32}$P, 3,000 Ci/mmol, Dupont NEN, Boston, Mass.) and purified by Nick columns (Amersham Pharmacia Biotech AB, Piscataway, N.J.). Hybridization and washings of the blots are performed as described by Engler-Blum, G., Meier, M., Frank. J., and Muller, G. A. Reduction of background in problems in non-radioactive Northern blot analysis enables higher sensitivity than 32P-based hybridizations. Anal. Biochem. 210, 235-244 (1993).

Library construction and screening. cDNA is synthesized from poly(A)$^+$ RNA isolated from pooled PBMCs of multiple LGL leukemia patients using oligo dT primer. The cDNA is unidirectionally inserted the EcoRI/XhoI sites of Lambda ZAPII (Stratagene).cDNA library is screened using EST according to standard protocol (Sambrook et al., 1989). In a preferred embodiment, DNA libraries are plated at a density of 50,000 plaque-forming units per 150 mm plate. Following incubation for 8 h at 37° C., the plated phage are overlaid with nitrocellulose filters. After 1 min the filters are removed and the membranes are crossed linked by Autocross linker. A [$^{32}$P] labeled cDNA fragment derived from an EST (GenBank accession No. N 47089) of interest is used to probe the filters. Hybridizations, washings, exposure of the membranes to films and then picking up the colony of interest are performed as outlined in the standard methodology (Sambrook et al., 1989). Secondary and tertiary screenings were also performed as outlined in standard methodology (Sambrook et al., 1989). After isolation of pure phage containing the gene of interest, mini-preparations or macro-preparation are made to isolate plasmid cDNA containing the gene of interest.

RT-PCR: To obtain the full-length sequence, 5' and 3' primers are designed based on the sequence information available in GenBank:

5' GCGCGGCCCAT GGAGTC 3'    (SEQ.ID # 1)

is used as forward primer and

5' CTTTTCTGTGTTCCCAAGC AGAAC GTCAAT 3'    (SEQ.ID # 2)

is used as reverse primer. Total RNA from PBMC isolated from LGL leukemia patients and normal healthy individuals is used as a template for reverse transcriptase for making cDNA using either oligo(dT) primer or random hexamer primers. The PCR reaction mixture is heated to 95° C. for 2 min and then cycled 40 times at 95° C. for 30 sec, 60° C. for 45 sec, and 72° C. for 1.5 min. Finally, the reaction mixture is heated at 72° C. for 7 min and stored at 4° C. The reaction product is electrophoresed in 1% agarose gels. For direct PCR, all the conditions are the same as above except that genomic DNA, isolated from PBMC, is used as a DNA template. PCR products are analyzed in 1% agarose gel and the bands are excised and cloned into a TOPO-TA cloning vector (Invitrogen) and sequenced. The insert is subcloned into EcoRI sites of mammalian expression vector pcDNA3.1 to produce pcDNA3S1P$_5$.

Cell culture and transfection. HEK293 cells are grown in Dulbecco's modified eagle's medium supplemented with 10% fetal bovine serum. The cells are transiently transfected with a plasmid encoding HA-tagged Erk2 (HA-Erk2) and either pcDNA 3 S1P$_5$ or pcDNA 3.1. Transfection is achieved by incubating the cells in 60 mm plates with plasmid/Lipofectamine complexes (2.1 µg total DNA/12 µl Lipofectamine) in serum-free medium for 5 hours. The DNA complexes are removed from the medium and the cells are starved overnight in serum-free medium and then used for experimentation.

Erk2 Kinase Assay. The serum-starved transiently transfected HEK293 cells are treated for 5 min preferably with either 1 µM sphingosine-1-phosphate (S1P) or with 1 µM lysophosphatidic acid (LPA). The cells are lysed in buffer containing 50 mM Tris-HCl pH 7.5, 150 mM NaCl, 1 mM EDTA, 1 mM EGTA, 1 mM DTT, 1% Triton X-100, 25 mM NaF, 5 mM sodium pyrophosphate, 20 mM ρ-nitrophenyl phosphate, 2 µg/mL leupeptin, and 100 µg/mL phenylmethylsulfonyl fluoride. HA-Erk2 is immunoprecipitated with the monoclonal antibody HA.11 (Convance, Richmond, Calif.). Half of the immunoprecipitate is used to determine Erk 2 activity and the other half is used for measuring Erk2 protein expression. For the kinase assay, immune complexes are incubated for 10 min at 30° C. in 40 µl of buffer containing 20 mM Hepes, pH 7.5, 10 mM MgCl$_2$, 1 mM dithiothreitol, 10 mM p-nitrophenyl phosphate, 40 µM ATP and 0.375 mg/mL myelin basic protein and 10 µCi of [γ-$^{32}$P] ATP (3000 Ci/mmol). The reaction is terminated with SDS-containing gel-loading buffer and the reaction mixtures are analyzed on 11% SDS-polyacrylamide gels. The gels are processed by autoradiography. The bands on the gels are quantitated with a Phosphorimager. Erk2 protein in the immunoprecipitate is determined by immunoblotting with a polyclonal antibody to Erk2.

EXAMPLES

Referring now to FIG. 1, approximately 50 genes are up-regulated in LGL leukemia, with balanced differential expression of between about 7.8 and about 2.0. In addition, one EST is particularly noteworthy that is up-regulated in LGL leukemia with balanced differential expression of 3.0 (GenBank Accession number N47089). A clone containing this EST is sequenced. The total length of the EST is approximately 300 base pairs. A search using Blast shows 100% homology with another EST (GenBank Accession No. AF088014) named as *homo sapiens* full length insert cDNA clone YY85D04. No other information regarding this EST is found in the literature. No open reading frame is found within this sequence. Northern blot analysis confirms that a gene related to EST (GenBank ID No. N47098) is upregulated in majority of LGL leukemia patients.

Using the microarray screening method, one LGL leukemia patient is compared with one normal healthy individual. To show the same pattern in a larger sample of patents, Northern blot analysis is performed. Total RNAs, isolated from the PBMC of normal healthy individuals and LGL leukemia patients, are used in Northern blots. Initially, a 300 base pair cDNA fragment is used as a probe in initial experiments. Up-regulation of EST is observed in all the LGL leukemia patients when compared to the normal healthy individuals.

This confirms the microarray results regarding EST expression. The probe hybridizes to a 2.2 kb transcript in the Northern Blots. (FIG.-2).

An LGL leukemia library is constructed from the mRNA isolated from the pooled PBMCs of the seven LGL leukemia patients. This library is screened to obtain full-length sequence of the gene. Approximately 15 positive clones are selected and the larger clones are sequenced. The largest clone is 1500 bp in length. Analysis using Blast indicates that this gene has 85% homology with Rat edg-8 (Im et al, 2000). All of the clones are missing 5' end of the gene. Blast search with htgs show 99% homology with the sequence present in chromosome 19. Based on the sequence information, primers are designed from the 5' end and from 3' end of the open reading frame of the gene. Three different products (1.5, 1.6, and 1.2 bp in length) are obtained using RT-PCR. These products are subjected to gel electrophoresis and bands are excised, cloned into TOPO-TA cloning vectors and sequenced. The largest PCR product contains the entire open reading frame (FIG. 3). The deduced amino acid sequence shows 85% homology with complete sequence of rat sphingosine 1-phosphate receptor edg-8 and nrg-1. (FIG. 4). Shorter bands are also identified. The shorter bands are excised, cloned, and sequenced. These clones are splice variants of sphingosine 1-phosphate receptor with deletions. They are herein termed "sphingosine 1-phosphate receptor-1" and "sphingosine 1-phosphate receptor-2" (FIGS. 5 & 6).

Figure 7:
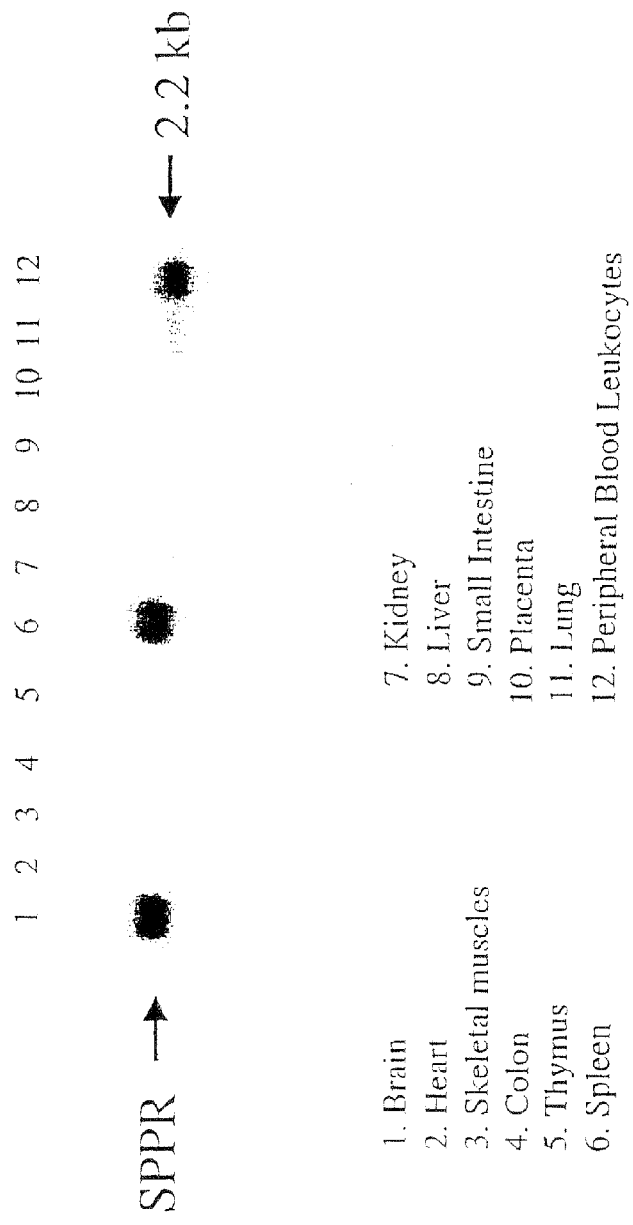
FIG. 7 shows results of sppr Northern blot analysis with different tissues. Northern blot analysis is performed using a multiple tissue Northern blot (Clontech). Northern blots contain approximately 1 ug of poly A+ per lane from twelve different human tissues. A 1.5 kb fragment containing the full-length open reading frame for sppr is used as a probe. Results show sppr is expressed in mainly brain, spleen, and peripheral blood leukocytes. Small amounts of sppr are also expressed in lung, placenta, liver and kidney.

Expression of sphingosine 1-phosphate receptor is examined in different normal tissues by Northern blot analysis. It is found that sppr is expressed in several tissues such as brain, spleen and PBMCs. (FIG. 7). Only trace amounts are detected in Jukat and CEM cell lines (data not shown).

To obtain a full-length sequence of the gene, an LGL leukemic cDNA library is constructed and screened using the EST probe. Approximately 15 positive clones are selected and larger clones are sequenced. The BLAST search of the largest clone (1500 bp) indicates that this gene has strong homology with Rat edg-8/Nrg-1. However, all of the clones are missing the 5' end of the gene when compared to the rat gene. A BLAST search with the human genome shows 99% homology with a sequence present on chromosome 19. Based on this sequence information, primers are designed from the 5' and 3' ends of the open reading frame of the gene.

Figure 10:
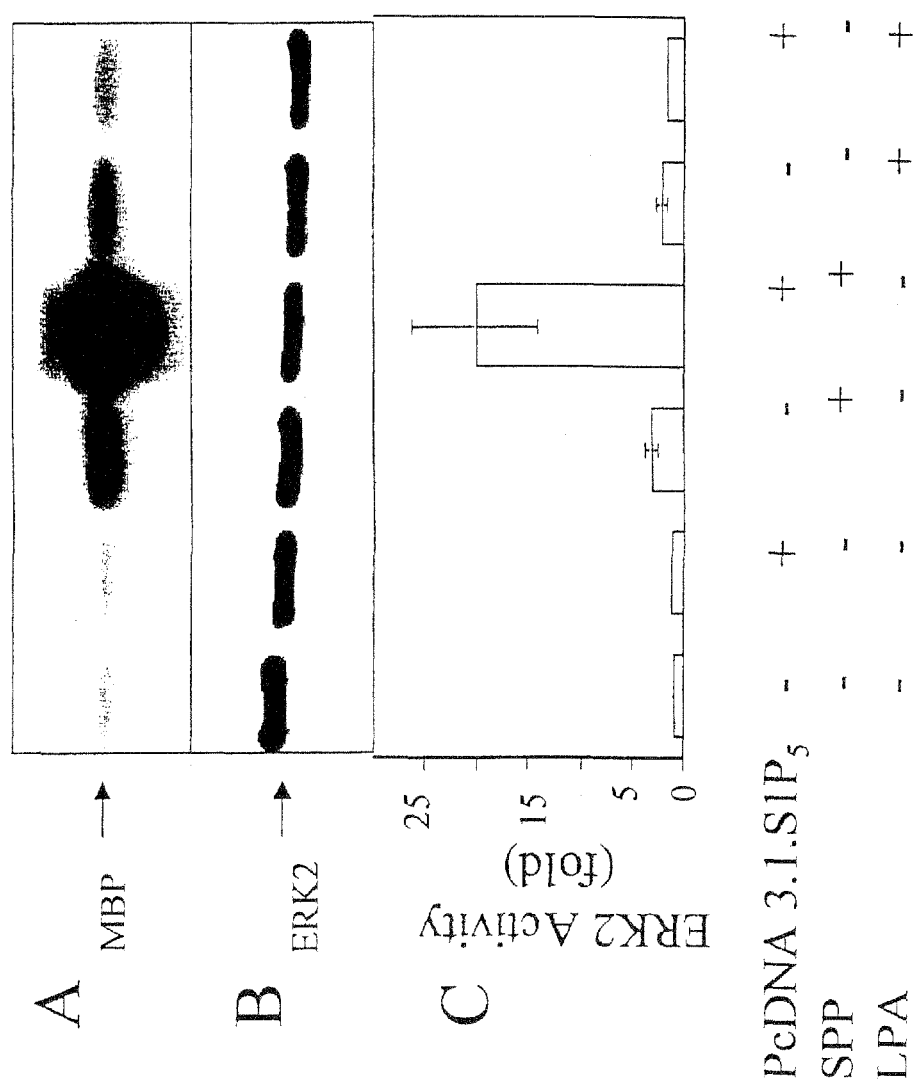
FIGS. 10A-10C show activation of Erk2 by S1P in HEK293 cells transiently transfected with $S1P_5$. HEK 293 cells transfected with the HA-ERK2 plasmid (0.2 μg) and either pcDNA $S1P_5$ (0.5 μg) or vector alone. Vector plasmid is added to each transfection reaction to equalize the amount of total DNA (2.1 μg). After serum-starvation, the cells are treated with 1 μM S1P or 1 μM LPA for 5 min (BSA was added to the controls). HA-ERK2 is immunoprecipitated from one half of each whole cell lysate and used for measuring the kinase activity utilizing MBP as substrate, while HA-ERK2 immunoprecipitated from the other half is used for determining the amount of ERK2 protein in the immune complex.

Three different RT-PCR products (1.5, 1.6, and 1.2 bp) are obtained. These products are subjected to gel electrophoresis. The resulting bands are excised and cloned into TOPO-TA cloning vectors and then sequenced. The largest PCR product contains a complete open reading frame. The nucleotide sequence and the deduced amino acids are shown in FIG. 8. The gene is designated as $S1P_5$ (see below). The nucleotide sequence shows very strong homology with G-protein coupled receptors, especially with the endothelial differentiation genes (EDGs). When the deduced amino acid sequence of the full-length sequence is aligned with other members of the family using the CLUSTALW (multi sequence alignment) program, it is approximately 26 to 44% identical and 58 to 72% similar with EDGs at amino acid level (Table 1). In addition, it shows 86% identity and 96% similarity with rat edg-8 or rat nrg-1 at amino acid level. (FIG. 9, Table I). Transient transfection of HEK293 cells with this gene results in activation of Erk2 activity in response to sphingosine-1-phosphate but not LPA, confirming that it is a sphingosine-1-phosphate receptor (FIG. 10). Therefore, this gene is named $S1P_5$.

Figure 11:
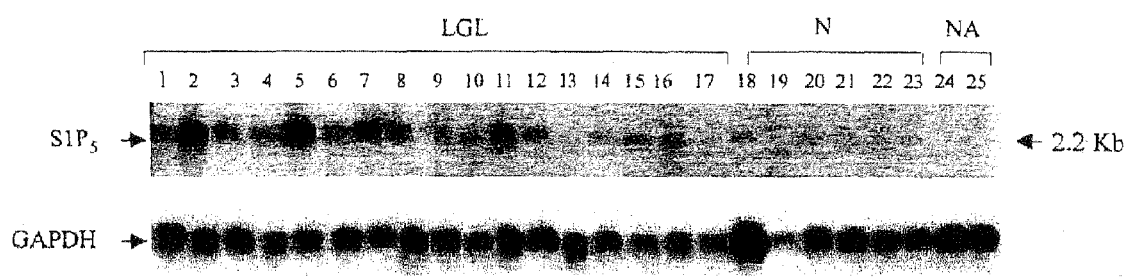
FIG. 11 shows Northern blot analysis of $S1P_5$ mRNA expression in PBMC of LGL leukemia patients and normal healthy individuals. Northern blot is performed with 10 μg of total RNA isolated from PBMC of LGL leukemia patients and normal healthy individuals. LGL=LGL leukemia patients, N=Normal healthy individual, NA=Normal healthy individuals PBMCs activated by IL2 and PHA. These results demonstrate over-expression of $S1P_5$ in the PBMC of LGL leukemia when compared to normal and normal activated. PBMC of healthy individuals.
Figure 13:
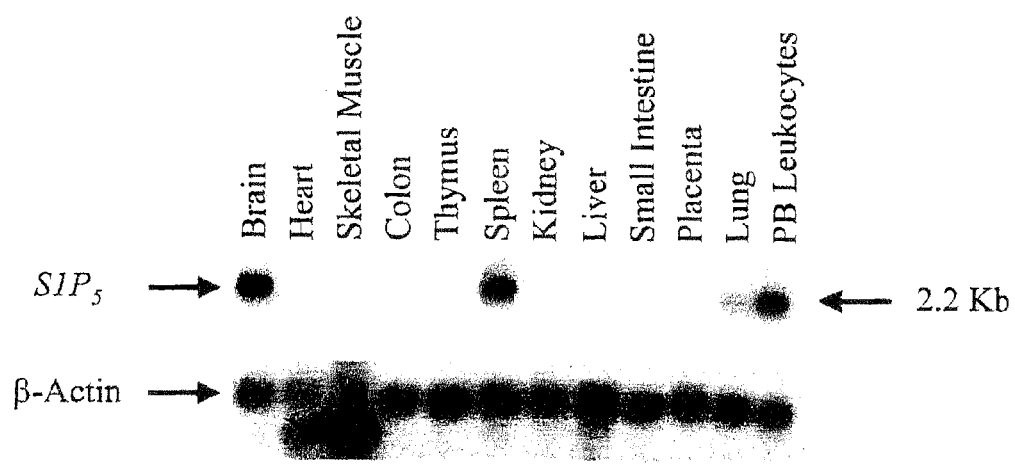
FIG. 13 shows tissue distribution of $S1P_5$ message. Northern blot analysis is performed using the multiple tissue blot obtained from Clontech. The Northern Blot contains approximately 2 μg of poly per lane from twelve different human tissues and a 1.5 kb fragment containing the full-length open reading frame of $S1P_5$ is used as a probe. As shown above, $S1P_5$ is expressed mainly in brain, spleen, and peripheral blood leukocytes. Trace amounts of $S1P_5$ are also expressed in lung, placenta, liver and kidney. (Please note: Signals are significantly stronger in normal tissue on poly A+RNA Northern blot compared to total RNA Northern blot.)

Samples from 30 LGL leukemia patients are tested for the presence of $S1P_5$ transcript by Northern blot analysis using full-length gene as a probe. Constitutive expression of $S1P_5$ transcripts is found in 24 samples (FIG. 11). In comparison $S1P_5$ transcripts are expressed at only trace levels in normal PBMC (N=12). After activation of normal PBMC the expression of $S1P_5$ is reduced to undetectable levels (FIG. 12). Additionally, expression of two smaller bands is detected in samples from leukemic LGL by RT-PCR. Human $S1P_5$ transcripts are expressed mainly in normal brain, spleen, and PBMC and in trace amounts in lung, kidney and liver (FIG. 13). Whereas expression of Edg-8 is observed only in brain and spleen of rat when Northern Blots are probed. Several cell lines are examined for the presence of $S1P_5$ transcript. Trace amounts of $S1P_5$ transcripts are identified in CEM and Jurkat cells (data not shown). All other cell lines tested are negative for $S1P_5$ transcript including MT2 (HTLV-I infected cell line) and MO-T (HTLV-II infected cell line), Moe7 (megakaryoblastic leukemic cell line) and U293 (human embryonic kidney cells).

TABLE 1

Identity and similarity between $SIP_5$ and other members of the Edgs. The deduced amino acid sequence of $SIP_5$ is aligned with the amino acid sequences of various members of Edgs. using the CLUSTALW program. Except for Edg 8 and nrg-1, all other sequences are from human. All the sequence information is obtained from GenBank.

| Name of the gene | % Identity | % Similarity |
| --- | --- | --- |
| hSiP5 | 100 | 100 |
| rEdg-8⁺ | 87 | 96 |
| rNrg-1 | 86 | 98 |
| h Edg-1⁺ | 44 | 72 |
| hEdg-5⁺ | 41 | 66 |
| h Edg-3⁺ | 40 | 70 |
| h Edg-6⁺ | 39 | 67 |
| h Edg-2☆ | 35 | 67 |
| h Edg-4☆ | 30 | 60 |
| hEdg-7☆ | 26 | 58 |

⁺ = Sphingosine 1-phosphate receptors
☆ = Lysophosphatidic acid receptors

Discussion

Leukemic LGL are resistant to Fas-induced apoptosis, in spite of over-expression of Fas and Fas-ligand (FasL) implying that the accumulation of circulating LGL can be due to dysregulation of apoptosis. The accumulation of circulating LGL in leukemic patients can also be due to clonal proliferation of LGL. In order to understand the molecular mechanisms involved in pathogenesis of LGL leukemia, microarray techniques are used to identify differentially expressed genes. Approximately 50 genes are identified that are up-regulated and 10 genes that are down regulated. Several ESTs are also identified which show differential expression. As a systematic study, one of the ESTs that is up-regulated in LGL Leukemia is characterized. The full-length gene is obtained by screening the LGL leukemia library and performing RT-PCR, which is 85% identical to the rat Sphingosine-1 Phosphate receptor. This gene belongs to G-protein coupled receptor super family and can act as a sphingosine-1-phosphate receptor. Several splice variants in LGL leukemia patients are also identified, and are named Sphingosine 1-phosphate receptor 1 and Sphingosine 1-Phosphate receptor 2. The deduced amino acid sequence of Sphingosine 1-Phosphate receptor with rat edg-8 or nrg shows 85% homology. It has seven transmembrane domains, which is a characteristic of GTP-coupled receptors. Thus, the Sphingosine-1 Phosphate is involved in the signal transduction from the sphingosine 1-Phosphate in human.

Although the gene has lot of homology with other members of edg family, it is preferably named sphingosine-1- phosphate receptor (S1P$_5$) because it is mainly present in lymphocytes, brain and spleen, but not in endothelial cells.

Lysophosphatidic acid (LPA) and sphingosine 1-phosphate (S1P) mediate T cell function. Both LPA and S1P signaling pathways are implicated in cell proliferation, suppression of apoptosis, enhancement of cellular survival and T-lymphoma cell invasion. Although it has been suggested that S1P can act as an intracellular mediator, it has also been suggested that S1P acts as an extracellular ligand for cell surface receptors. Indeed several such receptors have been identified in a wide variety of tissues. For example, receptors Edg-1, -3, -5, -6 and -8, are specific for S1P, whereas Edg-2, -4, and -7 are LPA specific. In normal lymphocytes, there is differential constitutive expression of receptors for LPA and S1P. CD4$^+$ cells express predominantly Edg-4, while CD8$^+$ cells appeared to lack receptors for LPA and S1P as only traces of Edg-2 and Edg-5 are detected. Human T cell tumors express many Edgs for both LPA and S1P.

Rat edg-8/nrg-1 is shown to be a sphingosine-1-phosphate receptor based on specific binding of radio-labeled S1P to cell membranes, inhibition of forskolin-induced cAMP accumulation, increased GTP binding ability and calcium mobilization studies. Even though these properties are adequate to classify edg-8/nrg-1 as a sphingosine-1-phosphate receptor, it seems surprising that this acne is different from other members of the human sphingosine-1-phosphate receptor family. For example, activation of EDG-1, -3, -5 and -6 by S1P leads to activation of Erk1/2 and induction of cell proliferation. In contrast S1P inhibited serum-induces activation of Erk1/2 and also inhibits the cell proliferation in CHO cells expressing EDG-8. The reasons for these differences are not known and might be due to species variation. As shown herein, S1P activates Erk2 in transiently tranfected HEK293 cells while lysophosphatidic acid does not, suggesting that S1P$_5$ is a sphingosine-1-phosphate receptor and participates in sphingosine 1-phosphate mediated signal transduction. A computational model of the Edg-1 receptor predicts that Glu$^{121}$ is essential for interaction with S1P [21]. The S1P receptors Edg-1, -3, -5 and -8 as well as S1P$_5$ share such an anionic residue.

Leukemic LGL are antigen driven CTL that survive in vivo, at least in part, because of defective apoptosis. For example, leukemic LGL express both Fas and Fas-ligand, but are resistant to Fas mediated death. It is noteworthy that S1P$_5$ gene transcripts are down regulated after activation of normal T cells. Leukemic cells are activated T cells. Based upon the results disclosed herein, constitutive expression of S1P$_5$ transcripts represents dysregulated expression. This dysregulated expression of S1P$_5$ may participate in protection of leukemic LGL from apoptosis.

Note: The full-length sequence was deposited in GenBank (Accession No. AF331840) on Dec. 22, 2000.

Throughout this application, various publications, including United States patents, have been referred to. The disclosures of these publications and patents in their entireties are hereby incorporated by reference into this application to more fully describe the state of the art to which this invention pertains.

While the invention has been described in terms of various preferred embodiments, those skilled in the art will recognize that various modifications, substitutions, omissions, and changes may be made without departing from the spirit of the present invention. Accordingly, it is intended that the scope of the present invention be limited solely by the scope of the following claims.

We claim:

1. A method of screening for rheumatoid arthritis, comprising screening a sample from a patient for over-expression of a nucleic acid molecule encoding the sphingosine 1-phosphate receptor (SPPR) protein, wherein said protein comprises the amino acid sequence of SEQ ID NO:3, and wherein over-expression of said nucleic acid molecule is indicative of rheumatoid arthritis.

2. The method of claim 1, wherein said screening comprises measuring the amount of SPPR protein in the sample.

3. The method of claim 1, wherein said screening comprises measuring the amount of mRNA of SEQ ID NO:4 in the sample.

4. A method of screening for large granular lymphocyte (LGL) leukemia, comprising screening a sample from a patient for over-expression of a nucleic acid molecule encoding the sphingosine 1-phosphate receptor (SPPR) protein, wherein said protein comprises the amino acid sequence of SEQ ID NO:3, and wherein over-expression of the nucleic acid molecule is indicative of LGL leukemia.

5. The method of claim 4, wherein said screening comprises measuring the amount of SPPR protein in the sample.

6. The method of claim 4, wherein said sample comprises blood.

7. A method of screening for large granular lymphocyte (LGL) leukemia in peripheral blood mononuclear cells (PBMC), comprising screening a sample of PBMC from a patient for over-expression of a nucleic acid molecule encoding the SPPR protein, wherein said protein comprises the amino acid sequence of SEQ ID NO:3, and wherein over-expression of the nucleic acid molecule is indicative of LGL leukemia.

* * * * *

UNITED STATES PATENT AND TRADEMARK OFFICE
CERTIFICATE OF CORRECTION

| | | |
|---|---|---|
| PATENT NO. | : 7,964,358 B2 | |
| APPLICATION NO. | : 12/879918 | |
| DATED | : June 21, 2011 | |
| INVENTOR(S) | : Thomas P. Loughran and Ravi Kothapalli | |

It is certified that error appears in the above-identified patent and that said Letters Patent is hereby corrected as shown below:

<u>Column 1,</u>
Line 36, "not hilly" should read --not fully--.

<u>Column 2,</u>
Line 17, "when compare to" should read --when compared to--.
Line 47, "renamed S1P5.
        DESCRIPTION OF THE FIGURES"
should read
    --renamed S1P5.
        BRIEF DESCRIPTION OF THE SEQUENCES
SEQ ID NO:1 is a forward primer used according to the subject invention.
SEQ ID NO:2 is a reverse primer used according to the subject invention.
SEQ ID NO:3 is the predicted amino acid sequence of the human sphingosine 1-Phosphate receptor (SPPR) cDNA of SEQ ID NO:4.
SEQ ID NO:4 is the complete nucleotide sequence of human sphingosine 1-Phosphate receptor (SPPR) cDNA.
SEQ ID NO:5 is the amino acid sequence of rat nrg-1.
SEQ ID NO:6 is the amino acid sequence of rat cdg-8.
SEQ ID NO:7 is the amino acid sequence of SPPR.
SEQ ID NO:8 is the deduced amino acid sequence of splice variant, sphingosine 1-phosphate receptor 1 of SEQ ID NO:9.
SEQ ID NO:9 is the nucleotide sequence of splice variant, sphingosine 1-phosphate receptor 1.
SEQ ID NO:10 is the amino acid sequence of the sphingosine 1-phosphate receptor (S1P).
SEQ ID NO:11 is the amino acid sequence of the sphingosine 1-phosphate receptor 1 ($S1P_1$).

Signed and Sealed this
Eleventh Day of October, 2011

David J. Kappos
*Director of the United States Patent and Trademark Office*

SEQ ID NO:12 is the deduced amino acid sequence of splice variant, sphingosine 1-phosphate receptor 2 of SEQ ID NO:13.

SEQ ID NO:13 is the nucleotide sequence of splice variant, sphingosine 1-phosphate receptor 2.

SEQ ID NO:14 is the amino acid sequence of sphingosine 1-phosphate receptor 2 ($S1P_2$).

SEQ ID NO:15 is the full-length (2.2 kb) nucleotide sequence of human S1P5 cDNA (Figure 8).

SEQ ID NO:16 is the deduced amino acid sequence of human S1P5 cDNA coding region (Figure 8).

SEQ ID NO:17 is the predicted amino acid sequence of S1P5 (Figures 12A and 12B).

SEQ ID NO:18 is the predicted amino acid sequence of S1P5-alpha (Figure 12A).

SEQ ID NO:19 is the predicted amino acid sequence of S1P5-beta (Figure 12B).

DESCRIPTION OF THE FIGURES--.

Column 3,
Line 14, "sppr is" should read --sppr (SEQ ID NO:7) is--.
Line 15, "rat edg-1 and nrg-1. There" should read
　　--rat edg-1 (SEQ ID NO:6) and nrg-1 (SEQ ID NO:5). There--.
Line 17, "sequence and" should read --sequence (SEQ ID NO:9) and--.
Line 18, "sequence of" should read --sequence (SEQ ID NO:8) of--.
Line 22, "sequence and" should read --sequence (SEQ ID NO:13) and--.
Line 23, "sequence of" should read --sequence (SEQ ID NO:12) of--.
Line 40, "$S1P_5$ is" should read --$S1P_5$ (SEQ ID NO:15) is--.
Line 44, "abbreviation. The" should read --abbreviation (SEQ ID NO:16). The--.
Line 50, "$S1P_5$ is" should read --$S1P_5$ (SEQ ID NO:7) is--.
Line 51, "rat edg-8 and nrg-1. There" should read
　　--rat edg-8 (SEQ ID NO:6) and nrg-1 (SEQ ID NO:5). There--.

Column 4,
Line 18, "shows comparison of" should read --shows comparisons of--.
Line 19, "$S1P_5$-β. The" should read
　　--$S1P_5$-β (SEQ ID NO:17, SEQ ID NO:18, SEQ ID NO:19, respectively). The--.
Line 22, "sequence. A" should read --sequence (SEQ ID NO:18). A--.
Line 27, "sequence. A" should read --sequence (SEQ ID NO:19). A--.
Line 33, "poly per" should read --poly A+ per--.
Line 40, "Northern blot.)

CERTIFICATE OF CORRECTION (continued)
U.S. Pat. No. 7,964,358 B2

Column 4,
Line 40, "Northern blot.)
  DETAILED DESCRIPTION OF THE INVENTION"
 should read
  --Northern blot.)
    FIGURE 14 shows a comparison of the amino acid sequences of the sphingosine-1-phosphate receptor (S1P) (SEQ ID NO:10) and the sphingosine-1-phosphate 1 receptor (S1P1) (SEQ ID NO:11).
    FIGURE 15 shows a comparison of the amino acid sequences of S1P (SEQ ID NO:10) and S1P2 (SEQ ID NO:14).
  DETAILED DESCRIPTION OF THE INVENTION--.
Line 53, "is represented" should read --are represented--.

Column 10,
Line 38, "Phosphorimager" should read --PhosphorImager--.
Line 61, "sample of patents" should read --sample of patients--.

Column 13,
Line 25, "this acne is" should read --this gene is--.

UNITED STATES PATENT AND TRADEMARK OFFICE
CERTIFICATE OF CORRECTION

PATENT NO. : 7,964,358 B2
APPLICATION NO. : 12/879918
DATED : June 21, 2011
INVENTOR(S) : Thomas P. Loughran and Ravi Kothapalli It is certified that error appears in the above-identified patent and that said Letters Patent is hereby corrected as shown below:

Column 1,
Line 36, "not hilly" should read --not fully--.

Column 2,
Line 17, "when compare to" should read --when compared to--.
Line 47, "renamed S1P5.
              DESCRIPTION OF THE FIGURES"
should read
       --renamed S1P5.
              BRIEF DESCRIPTION OF THE SEQUENCES
    SEQ ID NO:1 is a forward primer used according to the subject invention.
    SEQ ID NO:2 is a reverse primer used according to the subject invention.
    SEQ ID NO:3 is the predicted amino acid sequence of the human sphingosine 1-Phosphate receptor (SPPR) cDNA of SEQ ID NO:4.
    SEQ ID NO:4 is the complete nucleotide sequence of human sphingosine 1-Phosphate receptor (SPPR) cDNA.
    SEQ ID NO:5 is the amino acid sequence of rat nrg-1.
    SEQ ID NO:6 is the amino acid sequence of rat edg-8.
    SEQ ID NO:7 is the amino acid sequence of SPPR.
    SEQ ID NO:8 is the deduced amino acid sequence of splice variant, sphingosine 1-phosphate receptor 1 of SEQ ID NO:9.
    SEQ ID NO:9 is the nucleotide sequence of splice variant, sphingosine 1-phosphate receptor 1.

This certificate supersedes the Certificate of Correction issued October 11, 2011.

Signed and Sealed this
Twenty-seventh Day of March, 2012

David J. Kappos
*Director of the United States Patent and Trademark Office*

SEQ ID NO:10 is the amino acid sequence of the sphingosine 1-phosphate receptor (S1P).

SEQ ID NO:11 is the amino acid sequence of the sphingosine 1-phosphate receptor 1 (S1P$_1$).

SEQ ID NO:12 is the deduced amino acid sequence of splice variant, sphingosine 1-phosphate receptor 2 of SEQ ID NO:13.

SEQ ID NO:13 is the nucleotide sequence of splice variant, sphingosine 1-phosphate receptor 2.

SEQ ID NO:14 is the amino acid sequence of sphingosine 1-phosphate receptor 2 (S1P$_2$).

SEQ ID NO:15 is the full-length (2.2 kb) nucleotide sequence of human S1P5 cDNA (Figure 8).

SEQ ID NO:16 is the deduced amino acid sequence of human S1P5 cDNA coding region (Figure 8).

SEQ ID NO:17 is the predicted amino acid sequence of S1P5 (Figures 12A and 12B).

SEQ ID NO:18 is the predicted amino acid sequence of S1P5-alpha (Figure 12A).

SEQ ID NO:19 is the predicted amino acid sequence of S1P5-beta (Figure 12B).

DESCRIPTION OF THE FIGURES--.

Column 3,
Line 14, "sppr is" should read --sppr (SEQ ID NO:7) is--.
Line 15, "rat edg-1 and nrg-1. There" should read
 --rat edg-1 (SEQ ID NO:6) and nrg-1 (SEQ ID NO:5). There--.
Line 17, "sequence and" should read --sequence (SEQ ID NO:9) and--.
Line 18, "sequence of" should read --sequence (SEQ ID NO:8) of--.
Line 22, "sequence and" should read --sequence (SEQ ID NO:13) and--.
Line 23, "sequence of" should read --sequence (SEQ ID NO:12) of--.
Line 40, "S1P$_5$ is" should read --S1P$_5$ (SEQ ID NO:15) is--.
Line 44, "abbreviation. The" should read --abbreviation (SEQ ID NO:16). The--.
Line 50, "S1P$_5$ is" should read --S1P$_5$ (SEQ ID NO:7) is--.
Line 51, "rat edg-8 and nrg-1. There" should read
 --rat edg-8 (SEQ ID NO:6) and nrg-1 (SEQ ID NO:5). There--.

Column 4,
Line 18, "shows comparison of" should read --shows comparisons of--.
Line 19, "S1P$_5$-β. The" should read
 --S1P$_5$-β (SEQ ID NO:17, SEQ ID NO:18, SEQ ID NO:19, respectively). The--.
Line 22, "sequence. A" should read --sequence (SEQ ID NO:18). A--.
Line 27, "sequence. A" should read --sequence (SEQ ID NO:19). A--.
Line 33, "poly per" should read --poly A+ per--.

CERTIFICATE OF CORRECTION (continued)
U.S. Pat. No. 7,964,358 B2

Column 4,
Line 40, "Northern blot.)
  DETAILED DESCRIPTION OF THE INVENTION"
 should read
  --Northern blot.)
   FIGURE 14 shows a comparison of the amino acid sequences of the sphingosine-1-phosphate receptor (S1P) (SEQ ID NO:10) and the sphingosine-1-phosphate 1 receptor (S1P1) (SEQ ID NO:11).
   FIGURE 15 shows a comparison of the amino acid sequences of S1P (SEQ ID NO:10) and S1P2 (SEQ ID NO:14).
  DETAILED DESCRIPTION OF THE INVENTION--.
Line 53, "is represented" should read --are represented--.

Column 10,
Line 38, "Phosphorimager" should read --PhosphorImager--.
Line 61, "sample of patents" should read --sample of patients--.

Column 13,
Line 25, "this acne is" should read --this gene is--.